(12) United States Patent
Shturman

(10) Patent No.: US 8,353,923 B2
(45) Date of Patent: *Jan. 15, 2013

(54) ROTATIONAL DEVICE WITH ECCENTRIC ABRASIVE ELEMENT AND METHOD OF USE

(75) Inventor: Leonid Shturman, Nyon (CH)

(73) Assignee: Cardiovascular Systems, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/311,689

(22) Filed: Dec. 6, 2011

(65) Prior Publication Data

US 2012/0150207 A1 Jun. 14, 2012

Related U.S. Application Data

(63) Continuation of application No. 11/919,686, filed as application No. PCT/IB2006/051671 on May 25, 2006, now abandoned.

(30) Foreign Application Priority Data

May 26, 2005 (GB) .................................. 0510778.4

(51) Int. Cl.
*A61B 17/22* (2006.01)
*A61B 17/32* (2006.01)
(52) U.S. Cl. ........................................ 606/159; 606/170
(58) Field of Classification Search .................... 604/19, 604/22, 108, 159, 170, 180, 194, 200
See application file for complete search history.

*Primary Examiner* — Ryan Severson
*Assistant Examiner* — Ashley Cronin
(74) *Attorney, Agent, or Firm* — Winthrop & Weinstine, P.A.

(57) ABSTRACT

A rotational device for removing an occlusion from inside a tubular structure, the device comprising a drive shaft for insertion over a guidewire into a tubular structure and an abrasive element on the drive shaft having its centre of mass offset from a longitudinal axis of the drive shaft. A solid counterweight is disposed on the drive shaft spaced from the abrasive element and having its centre of mass offset from the longitudinal axis of the drive shaft so that the abrasive element moves in an orbital path around said axis to abrade an occlusion from inside the tubular structure when the drive shaft rotates around the guidewire.

24 Claims, 30 Drawing Sheets

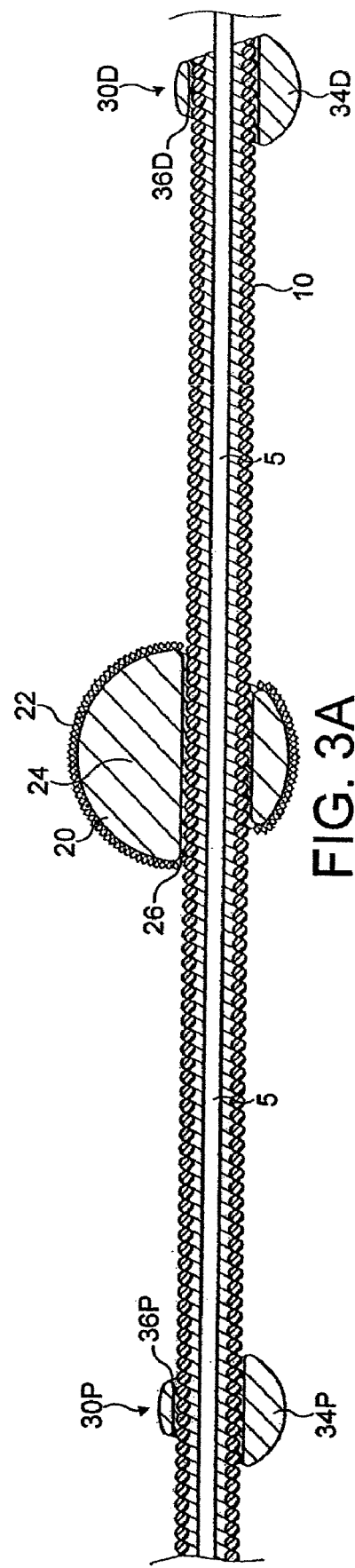

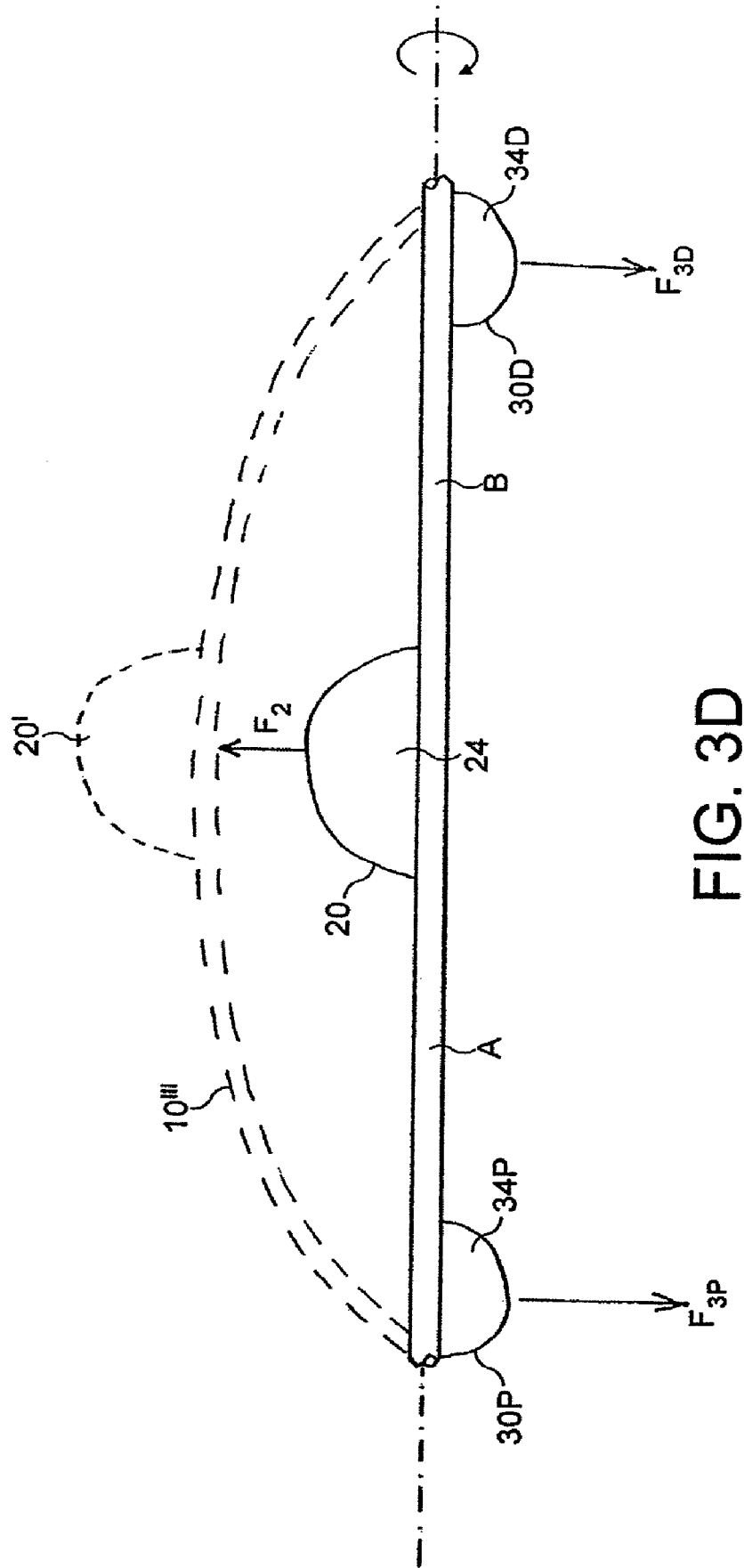

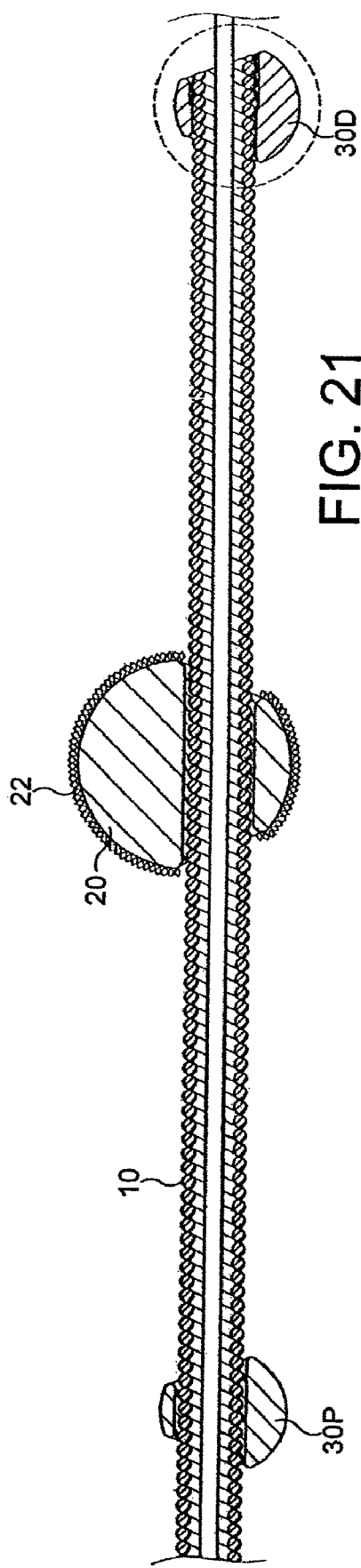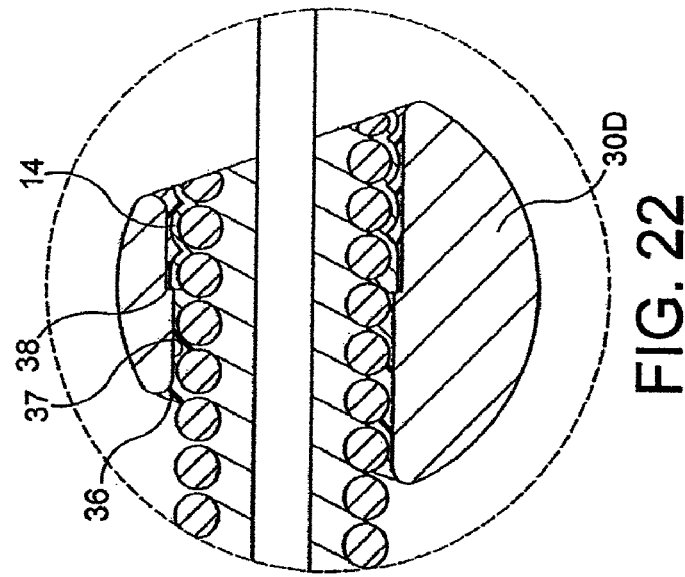

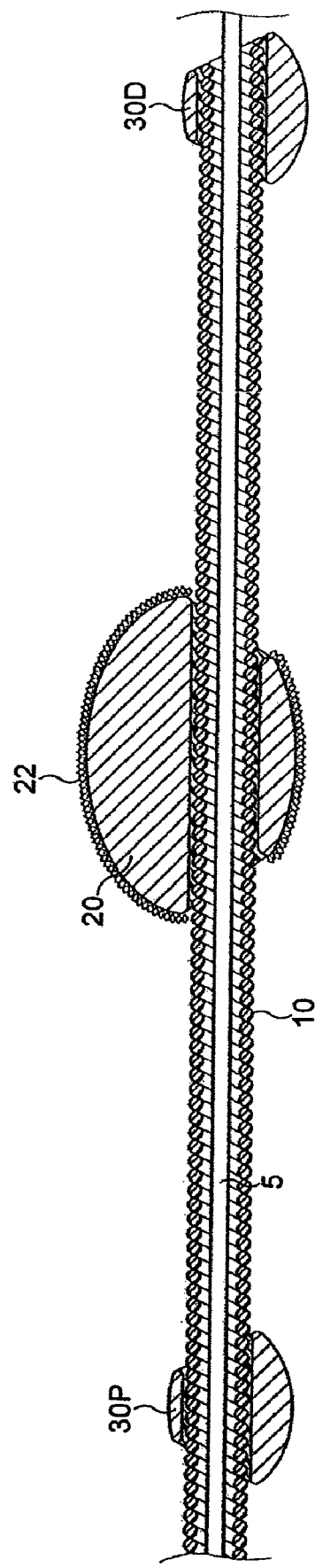

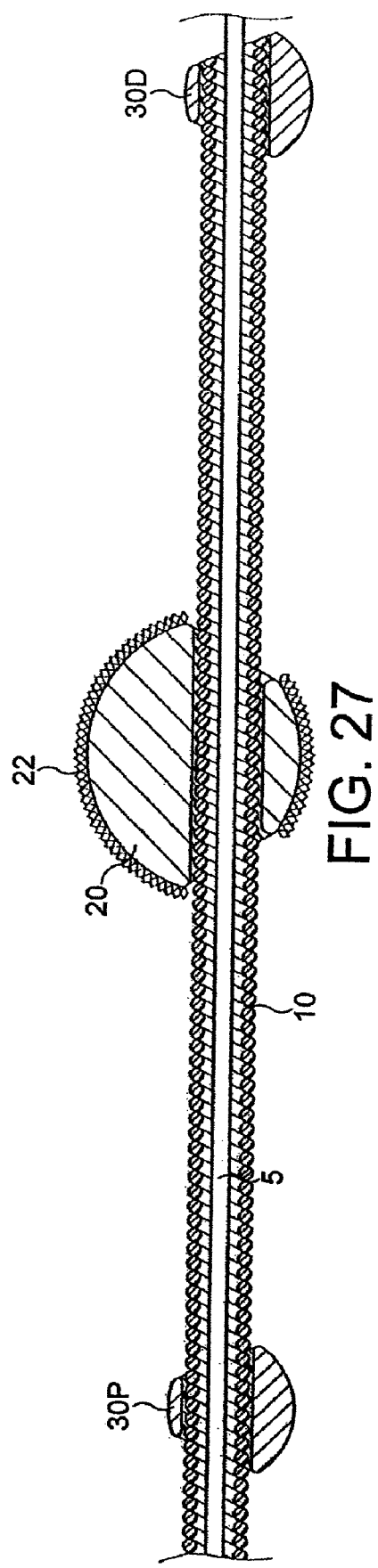

ROTATIONAL DEVICE WITH ECCENTRIC ABRASIVE ELEMENT AND METHOD OF USE

The invention relates to devices for removing material from the interior of tubular structures. More specifically, the invention relates to a device for removing or reducing occlusions, and other unwanted deposits from the interior of blood vessels or other tubular structures by rotating an abrasive element (e.g., burr) within the structure to partially or completely eliminate the unwanted material.

Atherosclerosis, the dogging of arteries, is a leading cause of coronary heart disease. Blood flow through the peripheral arteries (e.g., carotid, femoral, renal, etc.), is similarly affected by the development of atherosclerotic blockages. One existing method of removing or reducing blockages in blood vessels is known as rotational or ablative atherectomy. A long guidewire is inserted into the desired blood vessel and across the stenotic lesion, and a hollow drive shaft is advanced over the guidewire. The distal end of the drive shaft terminates in a burr provided with an abrasive surface such as diamond grit or diamond particles. The burr is positioned against the occlusion, and the drive shaft is rotated at extremely high speeds (e.g., 20,000-160,000 rpm). The abrasive surface of the burr scrapes against the occluding tissue and disintegrates it, reducing the occlusion and improving the blood flow through the vessel. Such a method and a device for performing the method are described in, for example, U.S. Pat. No. 4,990,134 to Auth, and U.S. Pat. No. 6,132,444 to Shturman (the instant inventor) et al. In the Shturman device, the abrasive element is located proximally to and spaced away from the distal end of the drive shaft.

In some systems, including the one described in U.S. Pat. No. 6,132,444 to Shturman et al, the abrasive element is formed as an eccentric mass positioned a short distance proximal from the distal end of the drive shaft. That is, the abrasive element may be circular, oval, or may have another shape in longitudinal cross section, however the center of mass (or center of gravity) of the abrasive element is not collinear with the rotational (longitudinal) axis of the drive shaft. The intention is that the eccentric mass, when rotated rapidly, will attempt to move away from the rotational axis and actually orbit around the rotational axis, thereby creating a much larger opening than the diameter of the abrasive element itself. However, in practice, such a system has significant limitations in opening stenotic lesions to a diameter substantially larger than that of the abrading element. Limitations in the swath of a single eccentric abrasive element manifest because of a tendency of the single eccentric abrasive element to rotate around its own center of mass which does not coincide with the guidewire around which the drive shaft is rotated. As a result, the rapidly rotating eccentric mass tends to force both the drive shaft and the guidewire to orbit a point which is relatively dose to the center of mass of the eccentric element. The limited maximum swath of an orbital abrasive device with a single eccentric element is explained by the single rapidly rotating eccentric mass pushing the guidewire in the direction 180° opposite the most effective area of the abrasive surface. Also, the entire assembly (abrasive element, drive shaft, and guidewire) has the tendency to vibrate during rotation in a less-than-perfectly-controlled fashion.

Accordingly, the present invention seeks to provide a rotational device for removing or reducing deposits from the interior of tubular structures, preferably biological structures such as arteries; veins, arteriovenous grafts, shunts, and the like.

The invention also seeks to provide a method and device for orbital angioplasty which reduces vibrations of the drive shaft.

It is known to provide a rotational device for removing an occlusion from inside a tubular structure, the device comprising a drive shaft for insertion into a tubular structure and an abrasive element on the drive shaft having its centre of mass offset from a longitudinal axis of the drive shaft.

A rotational device according to the present invention is characterised by a solid counterweight on the drive shaft spaced from the abrasive element and having its centre of mass offset from the longitudinal axis of the drive shaft so that the abrasive element moves in an orbital path around said axis to abrade an occlusion from inside the tubular structure when the drive shaft rotates.

It is also known to provide a rotational device comprising a drive shaft having a distal end section formed from at least one helically wound wire and an abrasive element on the distal end section having its centre of mass offset from a longitudinal axis of the drive shaft.

A rotational device according to the invention is also characterised by a solid counterweight on the distal end section spaced from the abrasive element and having its centre of mass offset from the longitudinal axis of the drive shaft.

In a preferred embodiment, the rotational device comprises two solid counterweights on the drive shaft. Preferably the rotational device includes a distal solid counterweight distal to the abrasive element on the drive shaft and, a proximal solid counterweight proximal to the abrasive element on the drive shaft.

Advantageously, the distance between the distal solid counterweight and the abrasive element and between the proximal solid counterweight and the abrasive element is substantially the same.

Preferably, the distal solid counterweight is disposed on the distal end of the drive shaft.

In an advantageous embodiment of the invention, the centre of mass of the or each solid counterweight is located in substantially the same longitudinal plane as the centre of mass of the abrasive element. Preferably, the centre of mass of the or each solid counterweight is diametrically opposite to the centre of mass of the abrasive element with respect to the longitudinal axis of the drive shaft. Most preferably, the centre of mass of the or each solid counterweight is separated from the centre of mass of the abrasive element by an angle of 180 degrees around the axis of the drive shaft.

Conveniently, the or each solid counterweight includes a shoulder that cooperates with a corresponding shoulder on the drive shaft to mount the or each solid counterweight to the drive shaft. Preferably, the shoulder on the drive shaft is formed from a layer of metal applied to the drive shaft.

The layer of metal applied to the drive shaft that cooperates with the or each solid counterweight may conform to the outer surface of the drive shaft.

In another embodiment, an adhesive layer is disposed between the or each solid counterweight and the drive shaft.

Preferably, the or each solid counterweight is rounded.

Advantageously, the or each solid counterweight is substantially spherical in shape. Alternatively, a longitudinal cross section of the or each solid counterweight is substantially elliptical in shape. Similarly, a longitudinal cross-section of the abrasive element may be substantially elliptical in shape.

solid counterweightIn a preferred embodiment, the or each solid counterweight is substantially half the weight of the abrasive element.

In the preferred embodiment, the or each solid counterweight is eccentrically disposed on the drive shaft.

The rotational device preferably includes a guidewire for insertion into a tubular structure prior to insertion of the drive shaft, the drive shaft being configured for insertion into the tubular structure over the guidewire.

According to another aspect of the invention, there is provided an atherectomy device for the removal of an occlusion from the interior wall of a blood vessel such as a coronary artery, bypass graft or other biological or non-biological tubular structure, comprising a rotational device according to the invention.

According to another aspect of the invention, there is provided a catheter for the removal of an occlusion from the interior wall of a biological structure comprising a rotational device according to the invention.

It is also known to provide a method of making a rotational device for removing an occlusion from inside a tubular structure, comprising a drive shaft for insertion into a tubular structure and an abrasive element on the drive shaft having its centre of mass offset from a longitudinal axis of the drive shaft.

A method of making a rotational device according to the present invention is characterised by the step of attaching a solid counterweight on the drive shaft spaced from the abrasive element and having its centre of mass offset from the longitudinal axis so that the abrasive element moves in an orbital path around said axis to remove an occlusion from the tubular structure when the drive shaft rotates.

In a preferred embodiment, the method includes the step of attaching two solid counterweights to the drive shaft.

Preferably, the method includes the step of forming corresponding shoulders on the drive shaft and on the or each solid counterweight that cooperate to mount the or each solid counterweight to the drive shaft.

Conveniently, the method of forming a shoulder on the drive shaft comprises the step of applying a layer of metal to the drive shaft. The method may include the step of gluing the solid counterweights to the drive shaft using adhesive. Alternatively, the method includes the step of soldering, welding or press-fitting the or each solid counterweight to the drive shaft.

The present invention also provides a method of using a rotational device to remove an occlusion from inside a tubular structure, comprising the steps of inserting a drive shaft with an abrasive element thereon into a tubular structure, the abrasive element having its centre of mass offset from a longitudinal axis of the drive shaft and, rotating the drive shaft so that a solid counterweight on the drive shaft having its centre of mass offset from the longitudinal axis of the drive shaft causes the abrasive element to move in an orbital path around said axis to abrade an occlusion from inside the tubular structure.

The rotational device preferably includes a guidewire and the method preferably includes the step of partially withdrawing the guidewire into the lumen of the drive shaft such that the distal end of the guidewire is located within the lumen of the drive shaft proximal to the distal end section of the drive shaft thereby making the distal end section of the drive shaft more flexible.

It is intended that, when the drive shaft of the rotational device according to the invention is rotated, centrifugal forces generated by the solid counterweights and the abrasive element preferably act in substantially the same plane but in opposite directions. These centrifugal forces cause the distal section of the drive shaft to flex and generally assume a bowed shape. As a result, the abrasive element, as well as both solid counterweights, move in orbital fashion around the axis of rotation of the drive shaft in orbits that are substantially larger than the respective diameters of the abrasive element or solid counterweights.

Pressure applied by the abrasive element and the solid counterweights to the tissue to be removed or to the inner surface of the vessel wall can easily be controlled by controlling the rotational speed of the drive shaft (i.e., the faster the speed of rotation, the greater the applied pressure), as well as by selecting the respective weights of the abrasive element and solid counterweights. Applied pressure is also affected by the distances between the abrasive element and the solid counterweights, since the distances affect the momentums which cause the drive shaft to bow.

As a result, the overall radial profile of the distal end section of the drive shaft in use is much larger than its motionless profile. The inventive device therefore can be used to abrade deposits formed on the entire inner surface of the wall or at least a greater portion of the inner surface of the wall of a tubular biological structure such as a blood vessel very efficiently. Yet despite the increased efficiency of the device, it may be easily inserted via a small arterial puncture or opening, because when the drive shaft is not rotated about its longitudinal axis, the distal end section of the drive shaft is substantially only as wide as the maximum width of its abrasive element or solid counterweights. Further, the provision of solid counterweights greatly reduces or eliminates unwanted vibration in the drive shaft during rotation.

It should be noted that the eccentric disposition of the abrasive element and solid counterweights is not limited to their geometrical eccentric position but, much more importantly, involves the eccentric disposition of their centers of mass with respect to the rotational axis of the drive shaft.

Embodiments of the invention will now be described, by way of example only, with reference to the accompanying drawings, in which:

FIG. 3A is a side sectional view of the distal end section of the orbital/rotational atherectomy device incorporating the invention taken along line 3-3 of FIG. 2.

FIG. 3D is a schematic of FIG. 3A illustrating the centers of mass and resultant forces which occur when the device is rotated and effect of these forces on the shape of the distal end section of the drive shaft.

FIG. 21 is a side sectional view of an embodiment of the invention showing structure attaching the distal solid counterweight to the drive shaft.

FIG. 22 is an enlarged side sectional view of the structure attaching the distal solid counterweight to the drive shaft of FIG. 21.

FIGS. 26 to 29 depict varying geometries of the eccentric abrasive element and solid counterweights for a device in accordance with the invention.

Figure 1:
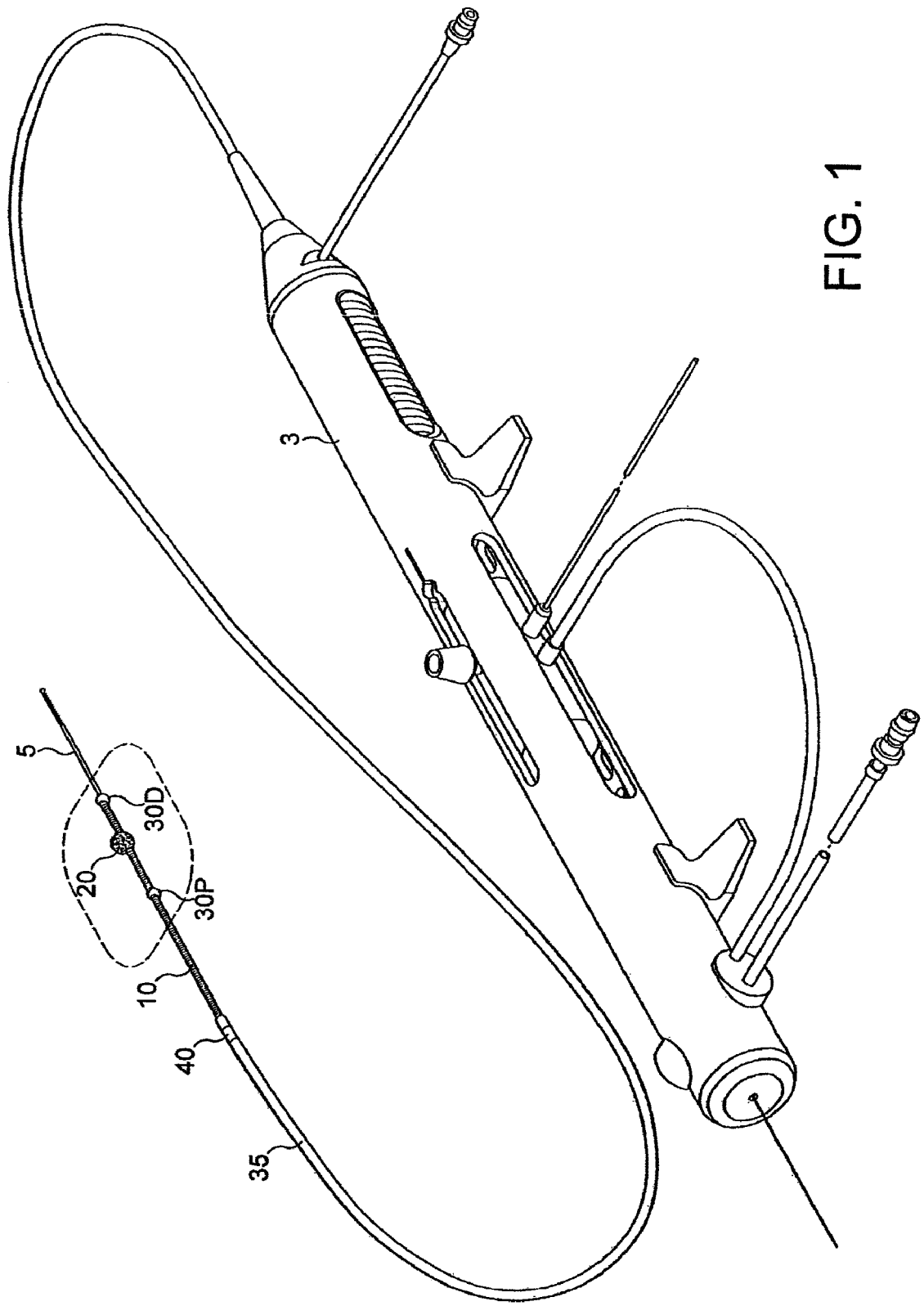
FIG. 1 is a perspective view of an orbital/rotational atherectomy device incorporating the invention.
Figure 2:
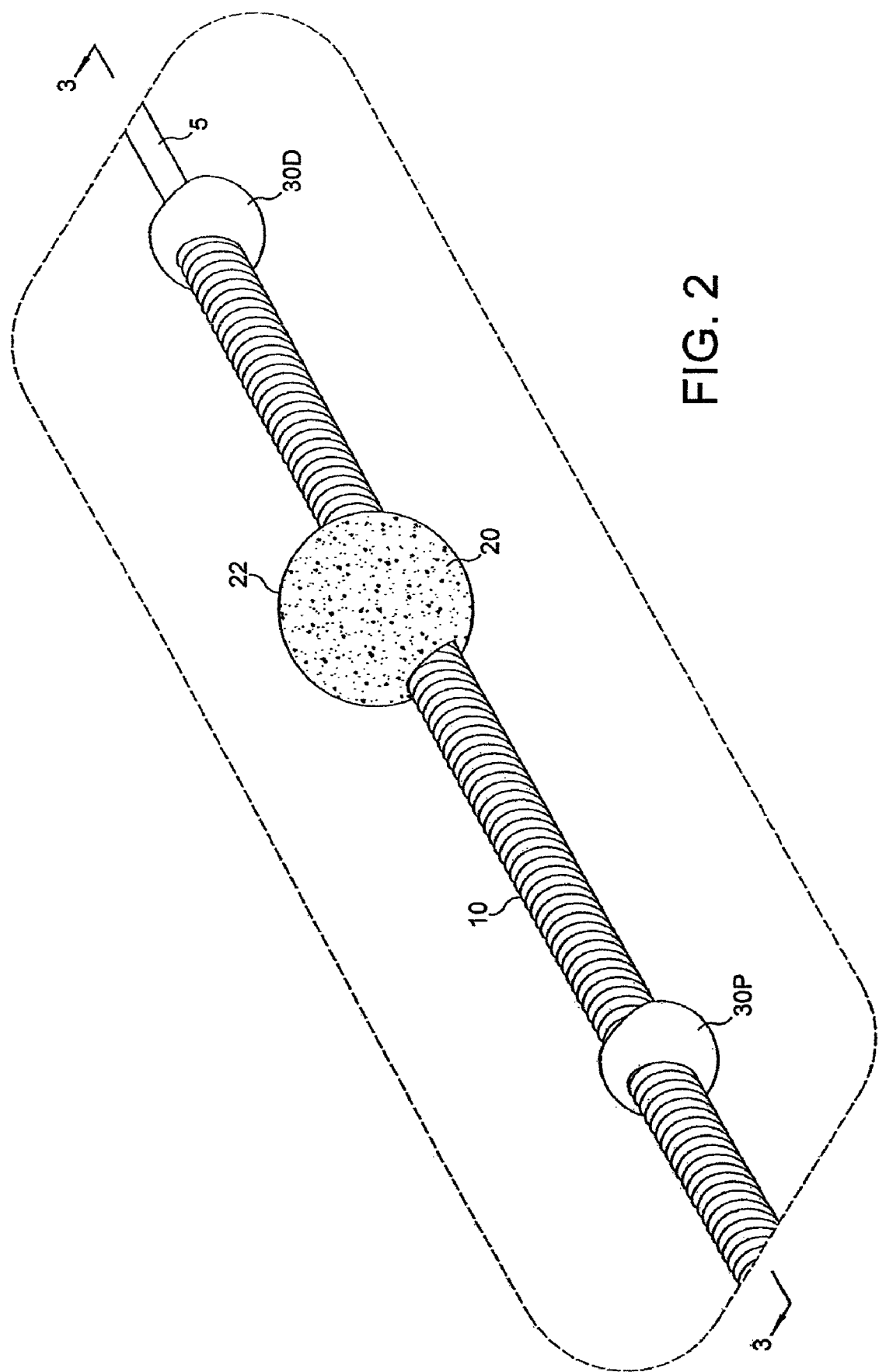
FIG. 2 is an enlarged view of the distal end section of the orbital/rotational atherectomy device incorporating the invention of FIG. 1.

FIG. 1 is a perspective view of a rotational atherectomy device in accordance with an embodiment of the invention. The advancer 3 is similar to that described in the Shturman patent mentioned above. It should be understood that any type of advancer may be used, including but not limited to advancers described by Auth, other advancers described by Shturman, and advancers developed by others. The instant improvements appear in the distal end section of the drive shaft and are outlined by the dashed line box of FIG. 1 and best illustrated in FIG. 2.

Drive shaft 10 is provided with an eccentric abrasive element or burr 20 on its distal end section at a predetermined distance from the terminus of the drive shaft. At or near the terminus of drive shaft 10 is disposed an eccentric solid counterweight 30D. Preferably, a second eccentric solid counterweight 30P is disposed on drive shaft 10 proximal to abrasive element 20. It is more preferable that the distance between solid counterweight 30P and abrasive element 20 is substantially equal to the distance between abrasive element 20 and solid counterweight 30D. As shown in FIG. 3A, abrasive element 20 is secured to drive shaft 10 via adhesive layer 26, and solid counterweights 30P and D are secured to drive shaft 10 via adhesive layers 36P and 36D, respectively. Abrasive element 20 has an abrasive surface 22, which may be formed by deposition of an abrasive material (e.g., diamond grit), or similar abrasive properties may be provided to the surface using laser, electrical discharge machining (EDM), or other methods of micro- or nano-machining.

Figure 3B:
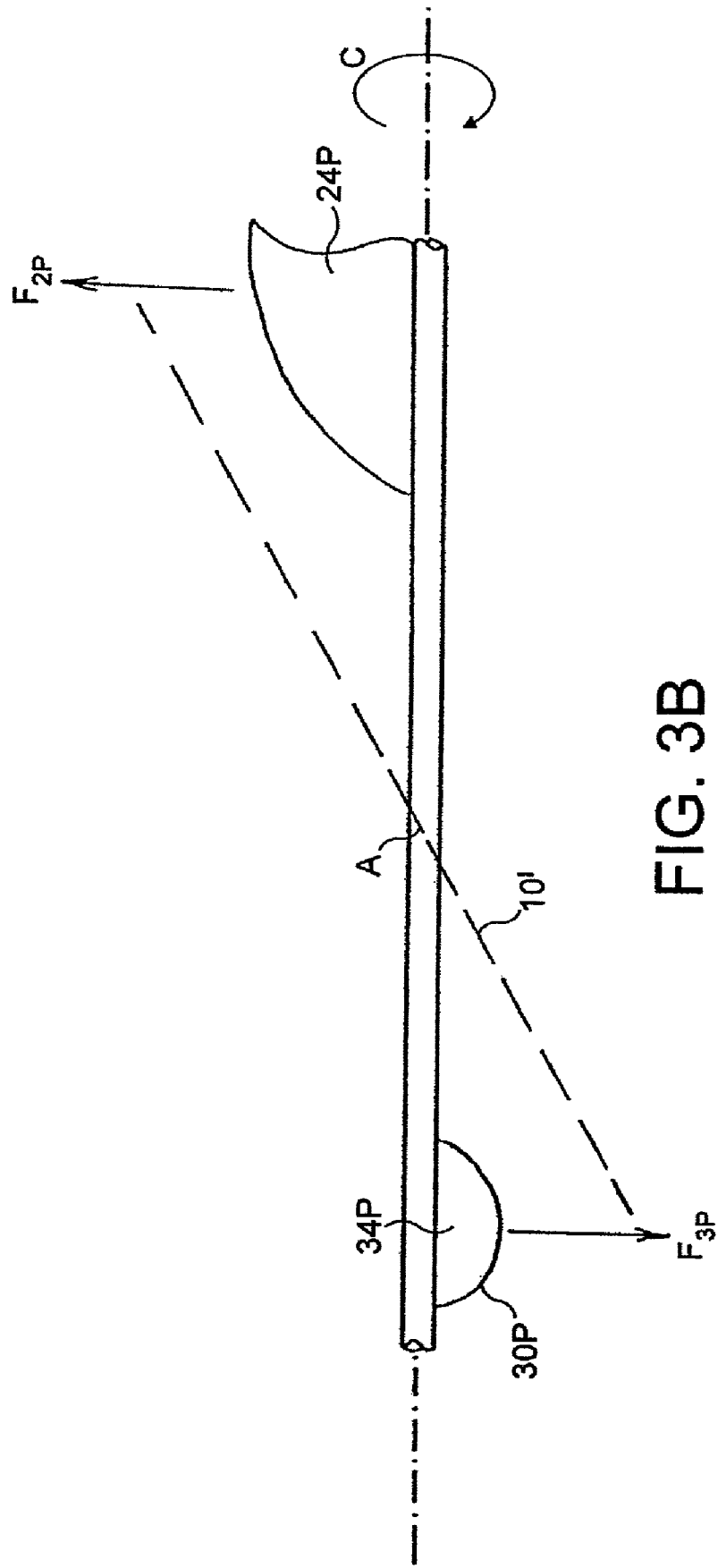
FIG. 3B is a schematic of the proximal side of FIG. 3A illustrating the centers of mass and resultant forces which occur when the device is rotated.

FIGS. 3A-D illustrate the inventive mass distribution of the instant device. None of eccentric abrasive element 20 or solid counterweights 30P or 30D is disposed on drive shaft 10 with its center of mass collinear with the drive shaft. As best shown in FIG. 3A, abrasive element 20 has a center of mass 24 which, in this configuration, is above drive shaft 10. Both solid counterweights have respective centers of mass 34P and 34D which, in this configuration, are below drive shaft 10. The references to "above" or "below" the drive shaft refer only to the illustration; the drive shaft is basically radially symmetrical and, conceptually, it is sufficient for the center of mass 24 to be "above" and the centers of mass of the solid counterweights 30 to be "below" the rotational axis of the drive shaft. That is, the centers of mass 34 of the solid counterweights 30 are preferably diametrically opposite that of abrasive element 20 (e.g., 180° around from the center of mass of the abrasive element 20 or thereabouts).

The significance of this weight distribution can best be explained with reference to FIGS. 3B-D. In FIG. 3B, the proximal portion of the distal end section of drive shaft 10 is shown. Point A is a central point (or center of mass) between solid counterweight 30P and abrasive element 20. Because center of mass 34P is on one side of drive shaft 10 and center of mass 24P (the center of mass of the proximal half of the abrasive element 20) is on the other side, rotation of drive shaft 10 in the direction of arrow C causes solid counterweight 30P to be pulled in the direction of arrow $F_{3P}$ and abrasive element 20 to be pulled in the direction of arrow $F_{2P}$. Both arrows $F_{3P}$ and $F_{2P}$ represent centrifugal forces acting in the same rotating longitudinal plane but in substantially opposite directions with respect to the rotational axis of the drive shaft. Accordingly, the section of drive shaft 10 shown in FIG. 3B tends to rotate about point A as shown by the dashed line 10'.

Figure 3C:
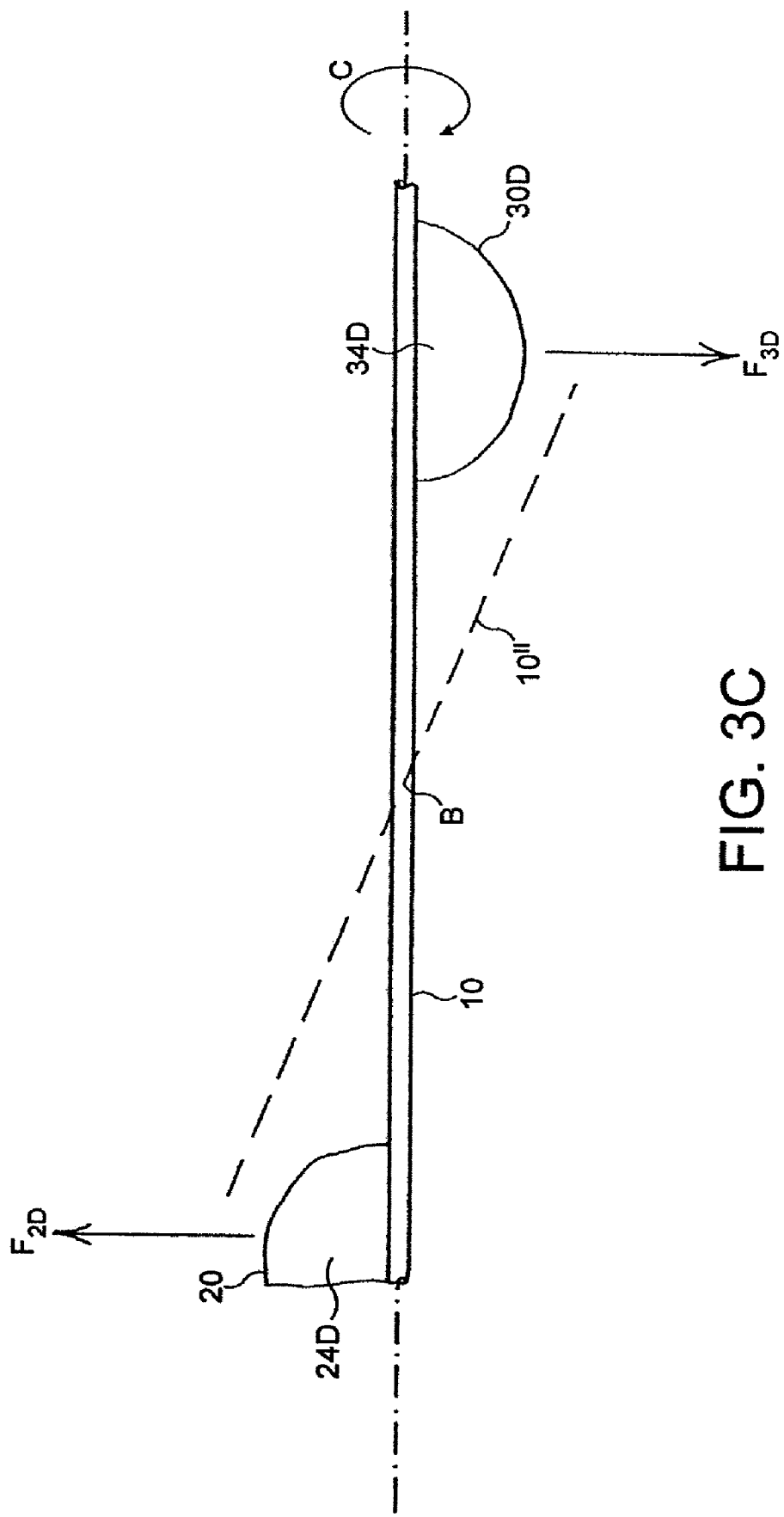
FIG. 3C is a schematic of the distal side of FIG. 3A illustrating the centers of mass and resultant forces which occur when the device is rotated.
Figure 4:
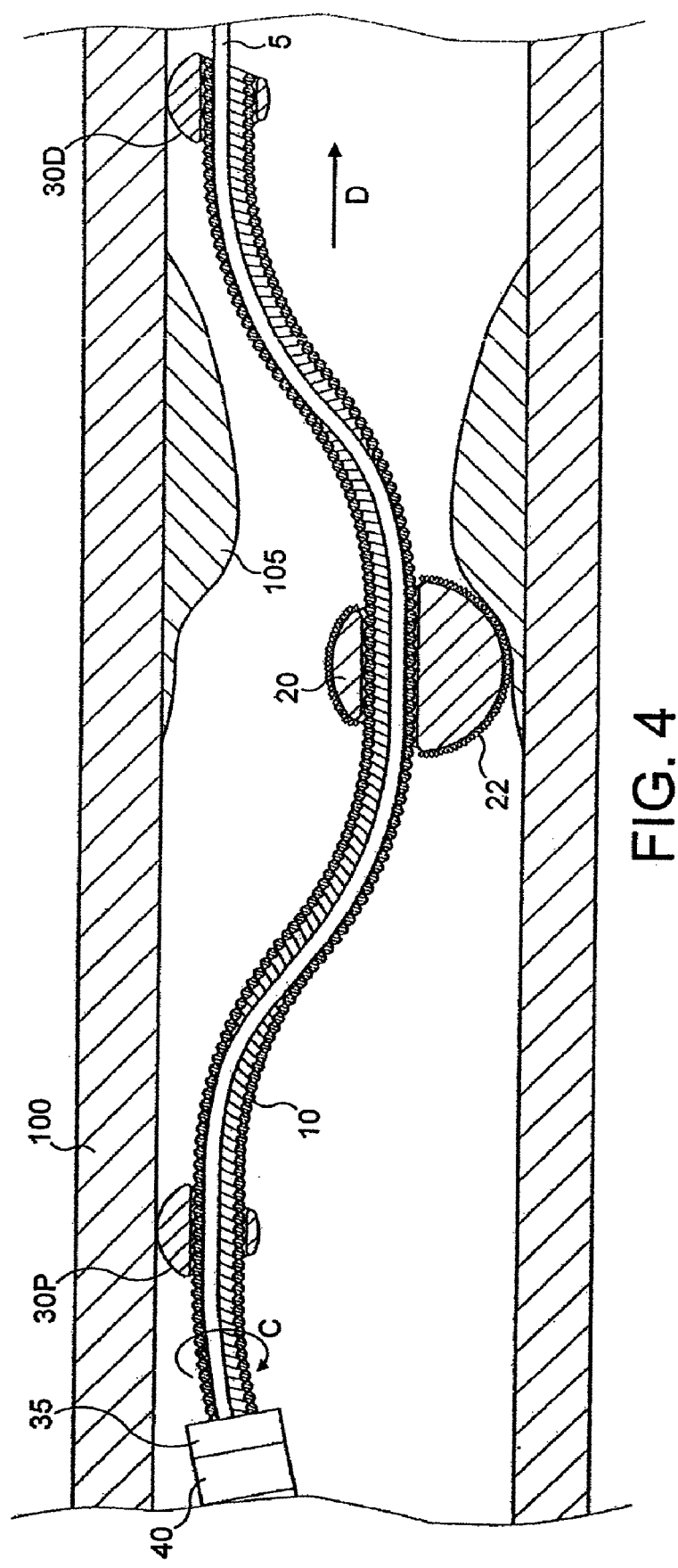
FIGS. 4-7 are successive sectional views of the rotating device according to the invention of FIG. 2 being moved over a guidewire and ablating deposits in a blood vessel.
Figure 5:
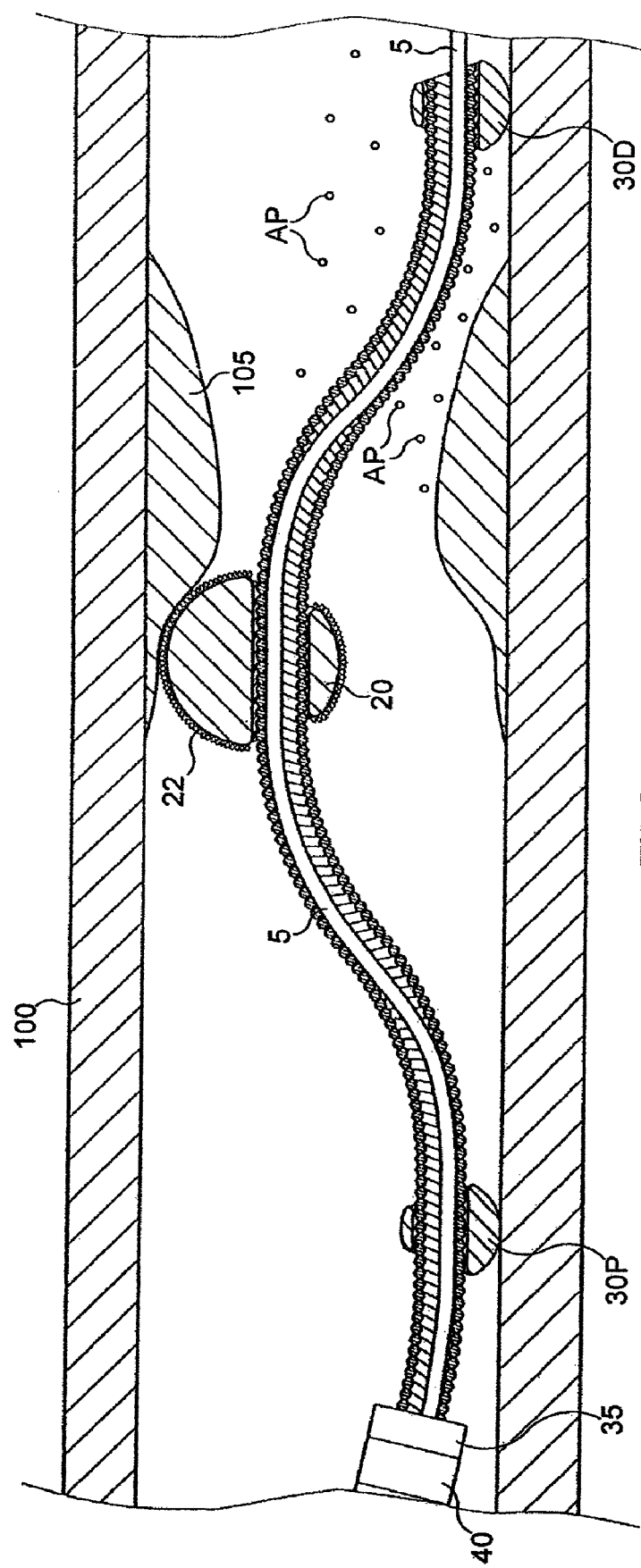
Figure 6:
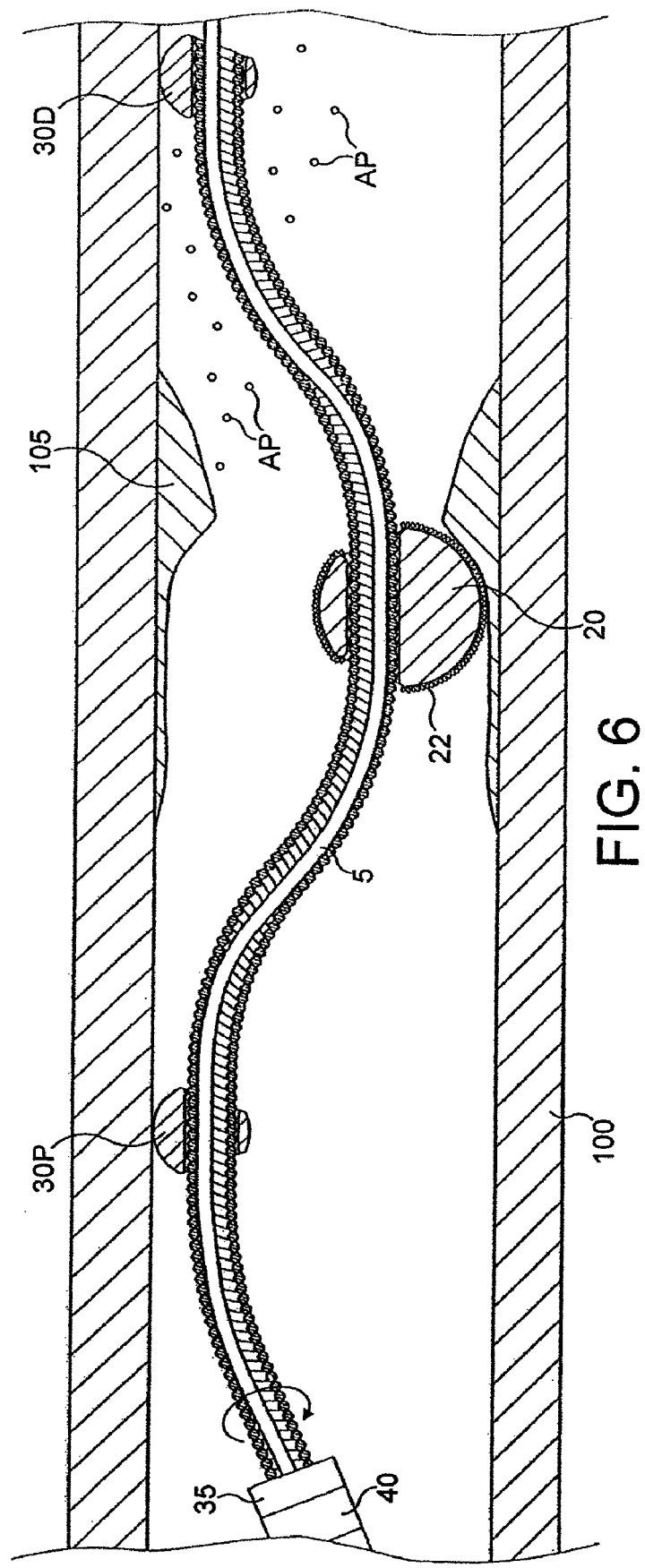
Figure 7:
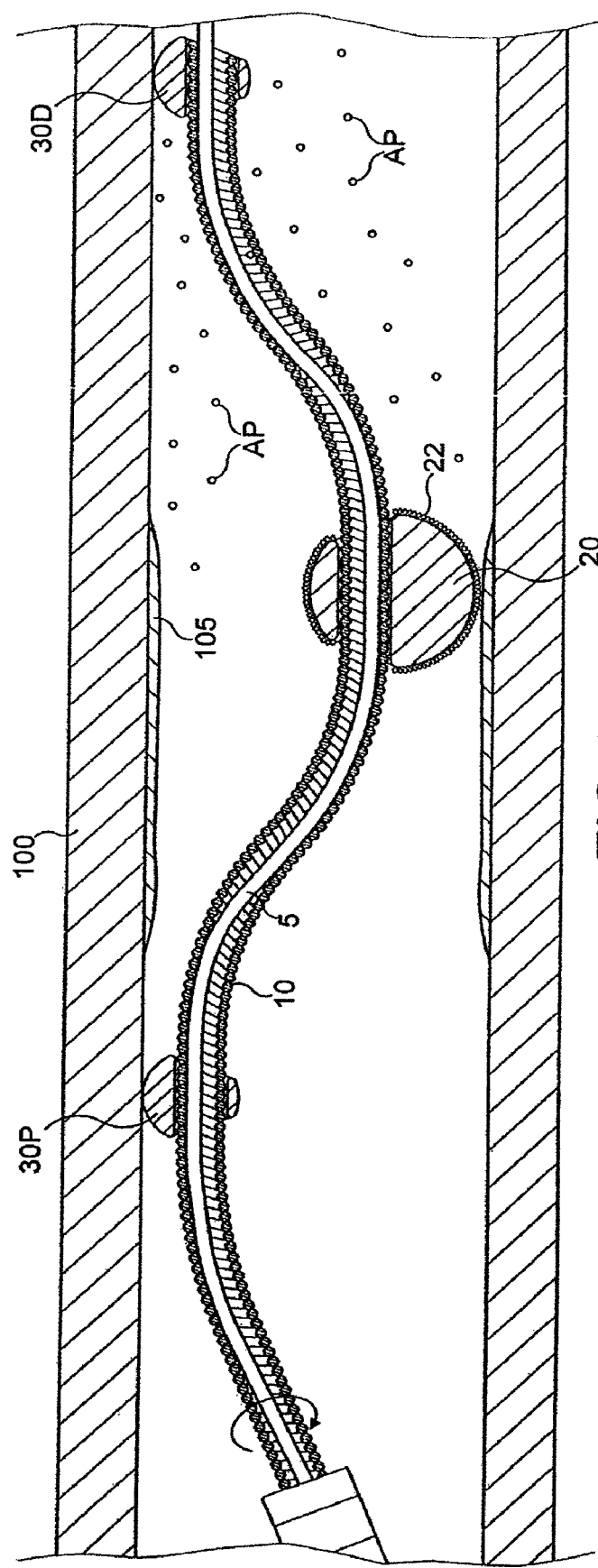
Figure 8:
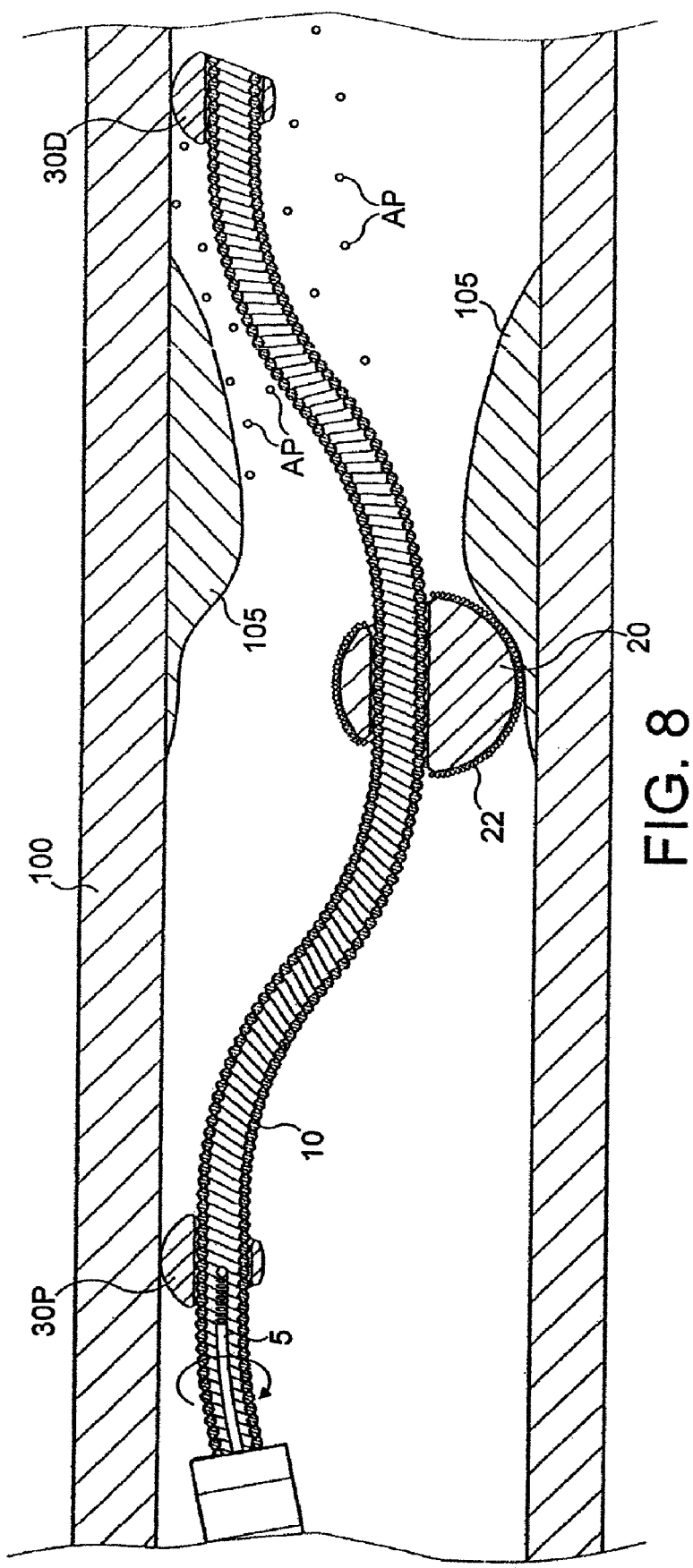
FIGS. 8-11 are successive sectional views of the rotating device according to the invention of FIG. 2 ablating deposits in a blood vessel when drive shaft is rotated around the guidewire which has been withdrawn into the lumen of the drive shaft such that the distal end of the guidewire is located within the lumen of the drive shaft proximal to the distal end portion of the drive shaft.
Figure 9:
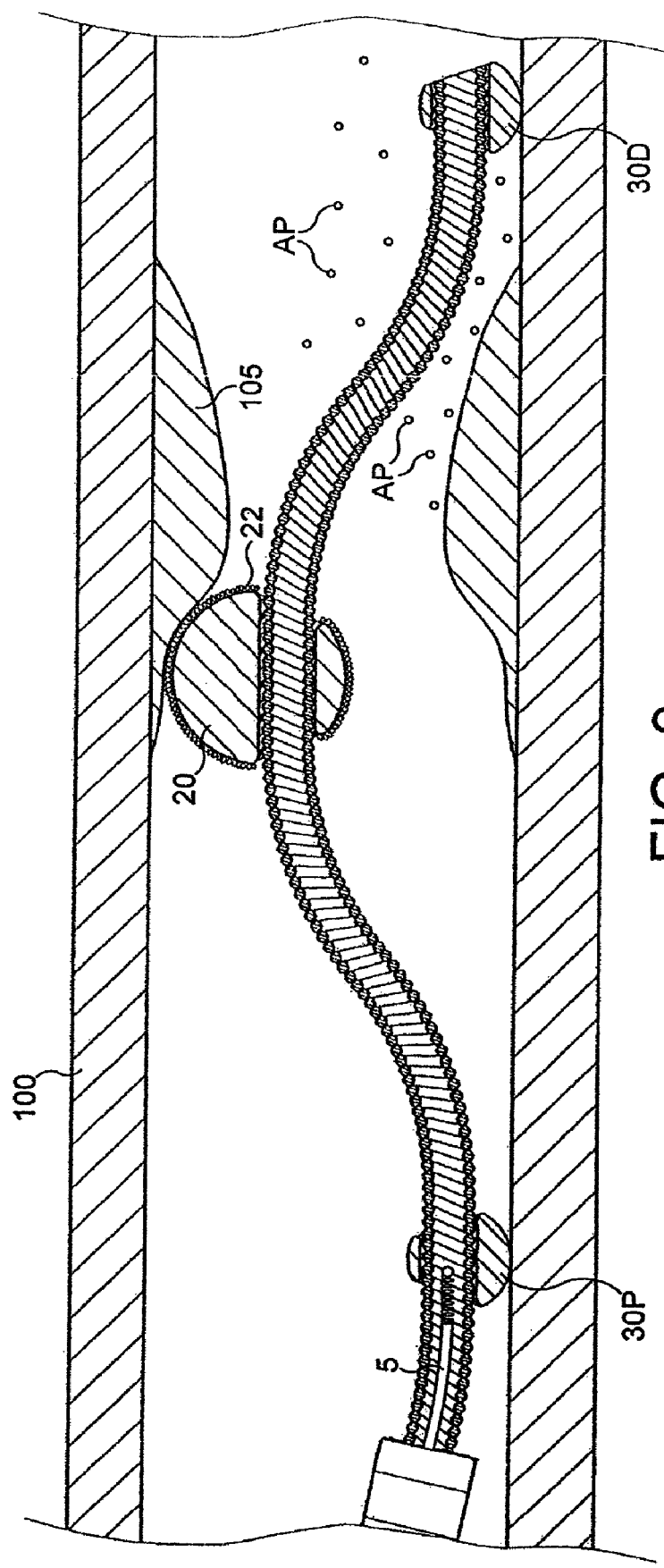
Figure 10:
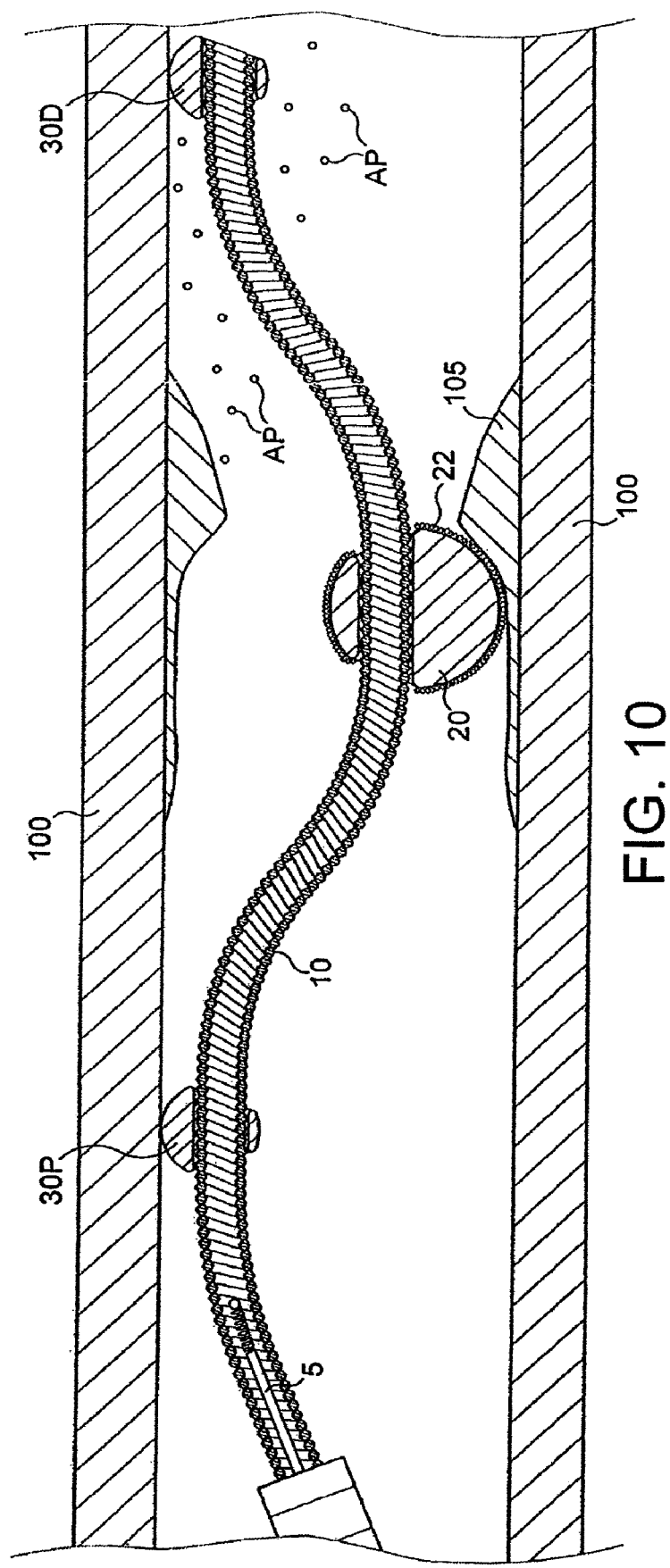
Figure 11:
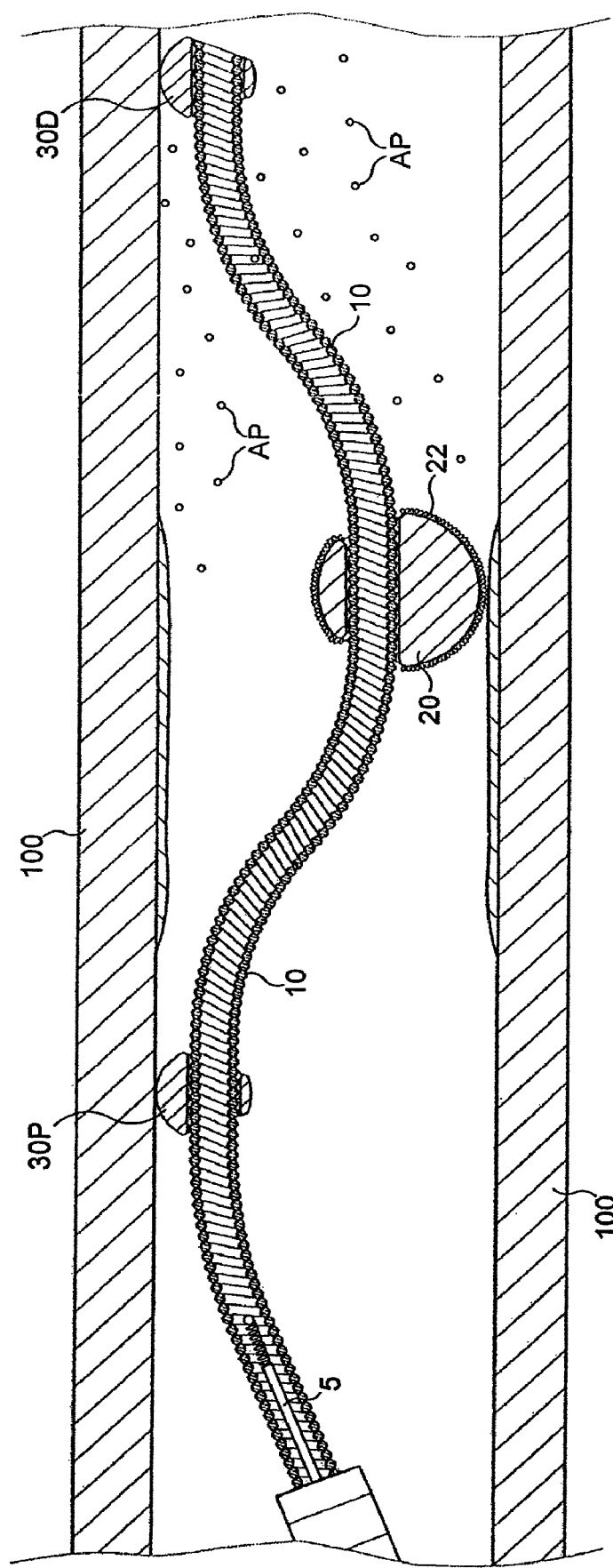

Similarly, in FIG. 3C, the distal portion of the distal end section of drive shaft 10 is shown. Point B is a central point between solid counterweight 30D and abrasive element 20. Because center of mass 34D is on one side of drive shaft 10 and center of mass 24D (the center of mass of the distal half of abrasive element 20) is on the other side, rotation of drive shaft 10 in the direction of arrow C causes solid counterweight 30D to be pulled in the direction of arrow $F_{3D}$ and abrasive element 20 to be pulled in the direction of arrow $F_{2D}$ as before. Accordingly, the section of drive shaft 10 shown in FIG. 3C tends to rotate about point B in the direction shown by the dashed line 10".

The combination of the two force diagrams FIGS. 3B and C is shown in FIG. 3D. Preferably, the centers of mass 34P and D of the solid counterweights 30P and D are disposed in the same radial position about drive shaft 10, and preferably that position is 180° around from the radial position of center of mass 24. When drive shaft 10 is rotated about its longitudinal axis, all three bodies disposed on drive shaft 10 cause the distal end section of drive shaft 10 to bow or flex with maximum deflection substantially at abrasive element 20 as shown by the dashed line 10'" and dashed outline of abrasive element 20'. (For the purpose of simplicity in FIG. 3D, only eccentric abrasive element 20 shown to be moving, rather than the abrasive element and the solid counterweights 30 moving in opposite directions.). As a result, instead of the path of the rotating abrasive surface 22 being limited to the maximum diameter of abrasive element 20, the path of abrasive surface 22 is greatly expanded and moves in orbital fashion within vessel 100.

The advantages of this expansion of the "reach" of the abrasive surface are readily understandable in view of FIGS. 4-7, which depict the invention being used to reduce a partial occlusion 105 of a blood vessel 100. In all of FIGS. 4-7, drive shaft 10 is being rotated within sheath 35 in the direction of arrow C and being advanced longitudinally within vessel 100 over guidewire 5 in the direction of arrow D. As drive shaft 10 is rotated, abrasive element 20 bows outward from the axis of rotation toward the wall of vessel 100, thereby increasing the overall swath that may be abraded by the device. In the first half of a rotation (FIG. 4), abrasive element 20 abrades against a lower portion of occlusion 105 in vessel 100. In the second half of a rotation (FIG. 5), abrasive element 20 abrades against an upper portion of occlusion 105 in vessel 100. In this way, the device can abrade the entire interior circumferential surface of the vessel 100, removing a thin layer of tissue as it is moved along the occlusion. Multiple forward and backward passes may be needed to reduce or remove the occlusion safely. Abraded particles (AP) in this embodiment of the invention travel distally along the treated vessel together with flow of flushing fluid, blood or radiopaque solution. Abraded particles may vary in size depending on size of particles forming abrasive surface of the abrasive element, rotational speed of such abrasive element and, most importantly, the degree of uniformity of the stenotic tissue which is being removed. The less uniform is the stenotic tissue, the higher the probability that larger size particles may be produced by the rotating abrasive element and travel distally along the treated vessel. For example, irregularly calcified stenotic tissue is expected to produce abraded particles (AP) of larger size. Radiopaque solution may be injected into the treated vessel after each pass or several passes in order to appreciate progress of tissue removal and assure safety of the procedure. The position of the distal end of the sheath 35 may be better visualized by placing radiopaque marker 40 at the distal end of the sheath 35.

FIGS. 8-11 depict essentially the same process as FIGS. 4-7 but in which the guidewire 5 has been withdrawn into the lumen of the drive shaft such that the distal end of the guidewire is located within the lumen of the drive shaft proximal to the end section of the drive shaft, thereby Acing the distal end section of the drive shaft more flexible.

Figure 12:
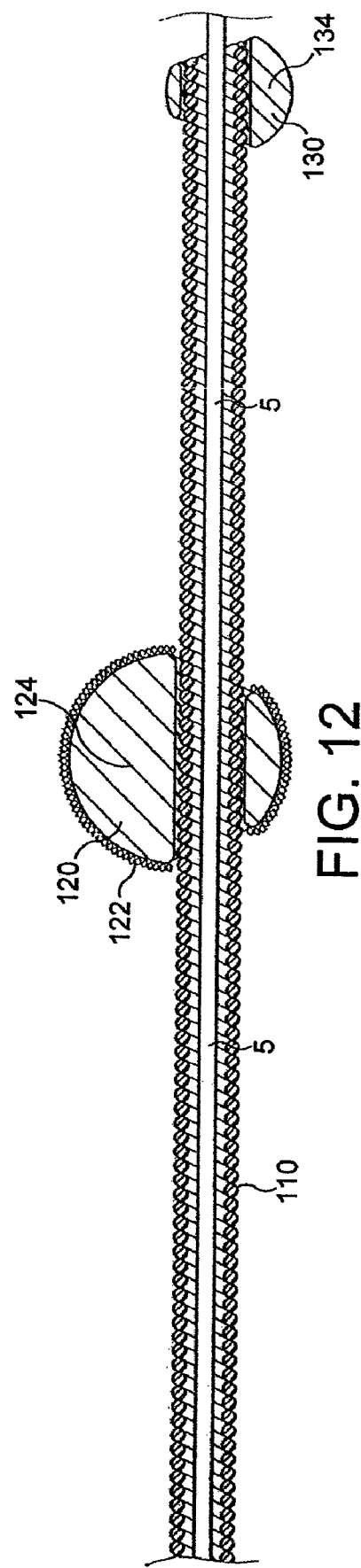
FIG. 12 is a sectional view of an alternate embodiment of the invention having a single distal solid counterweight.
Figure 13:
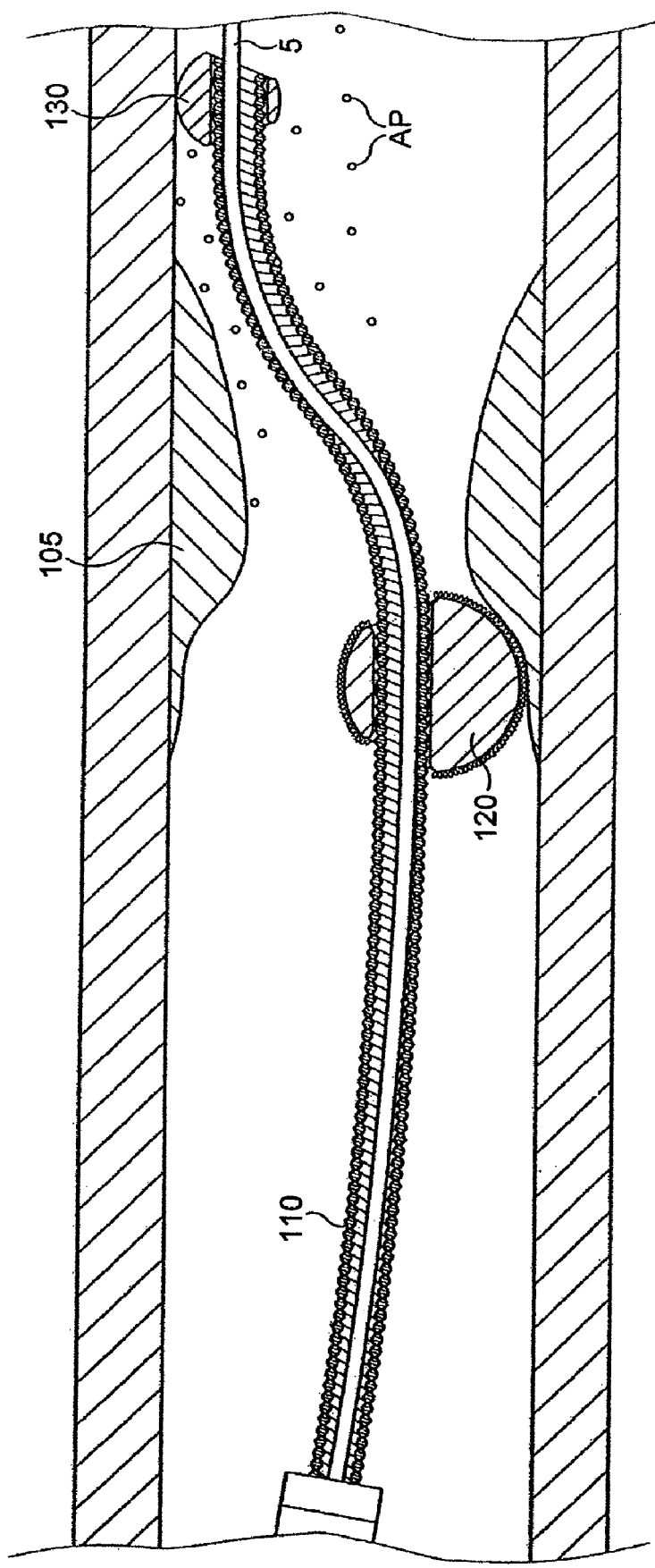
FIGS. 13-16 are successive sectional views of the device according to the invention of FIG. 12 when the drive shaft has been advanced over a guidewire and ablating deposits in a blood vessel.
Figure 14:
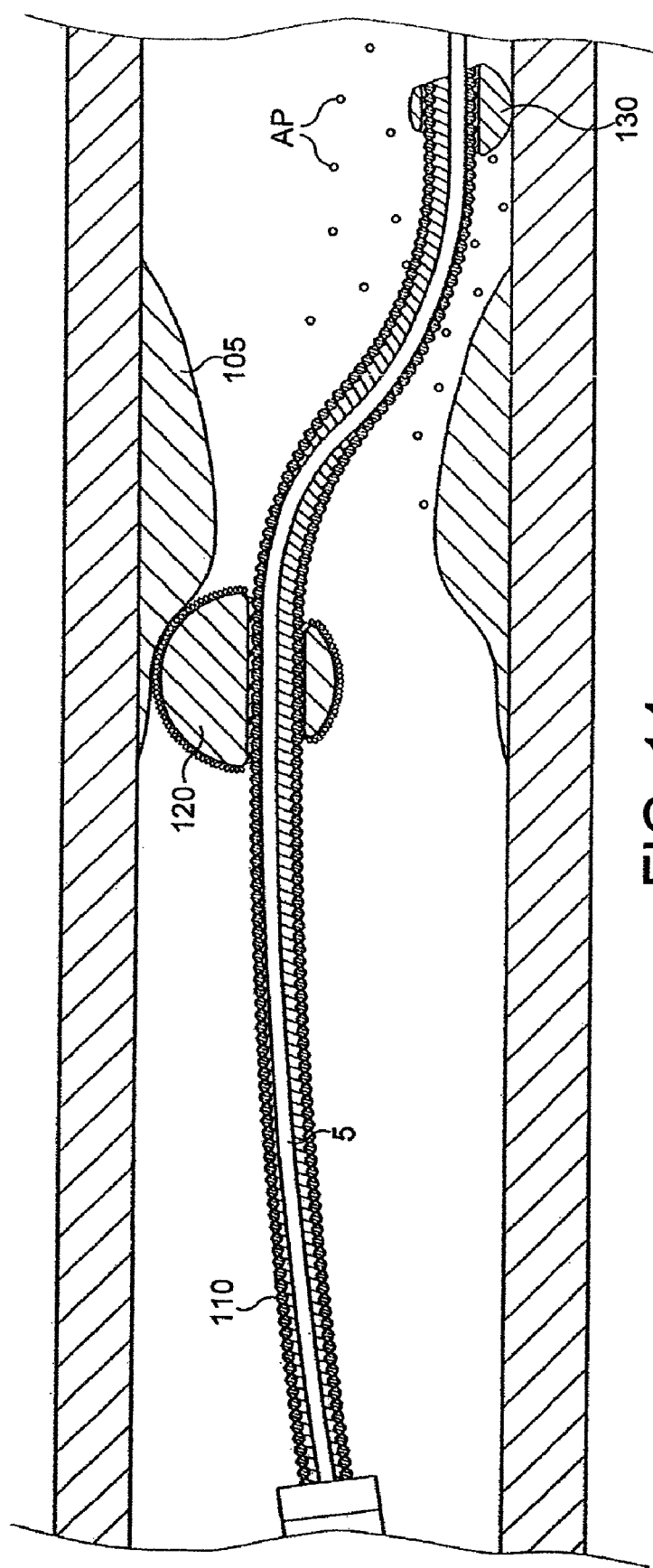
Figure 15:
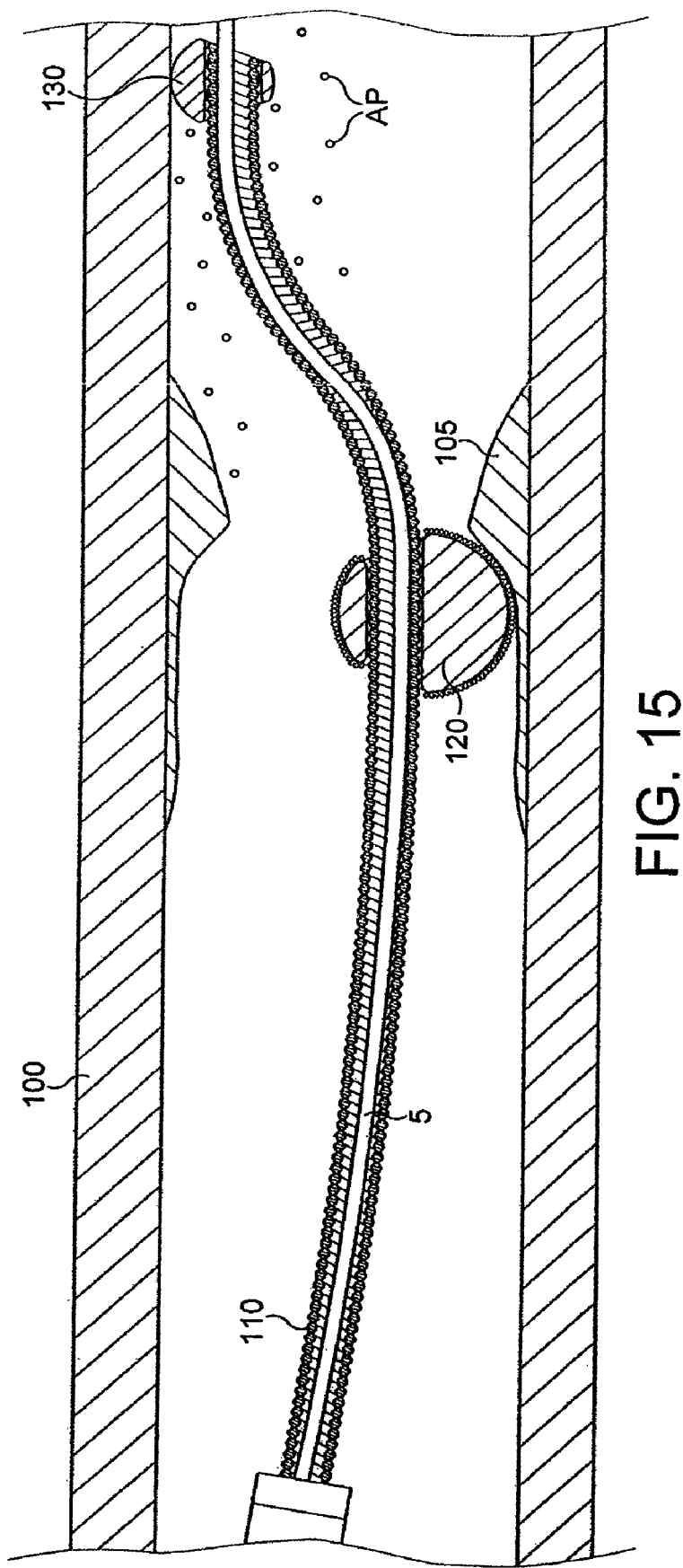
Figure 16:
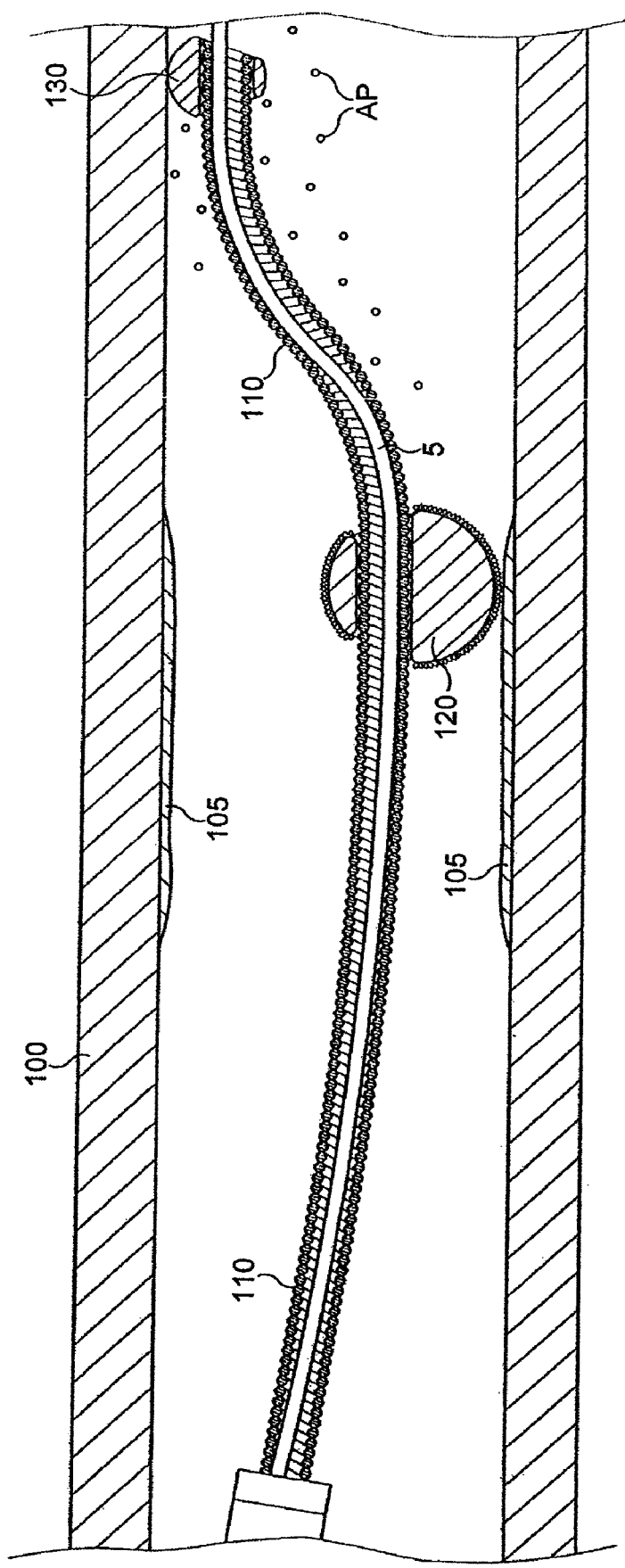
Figure 17:
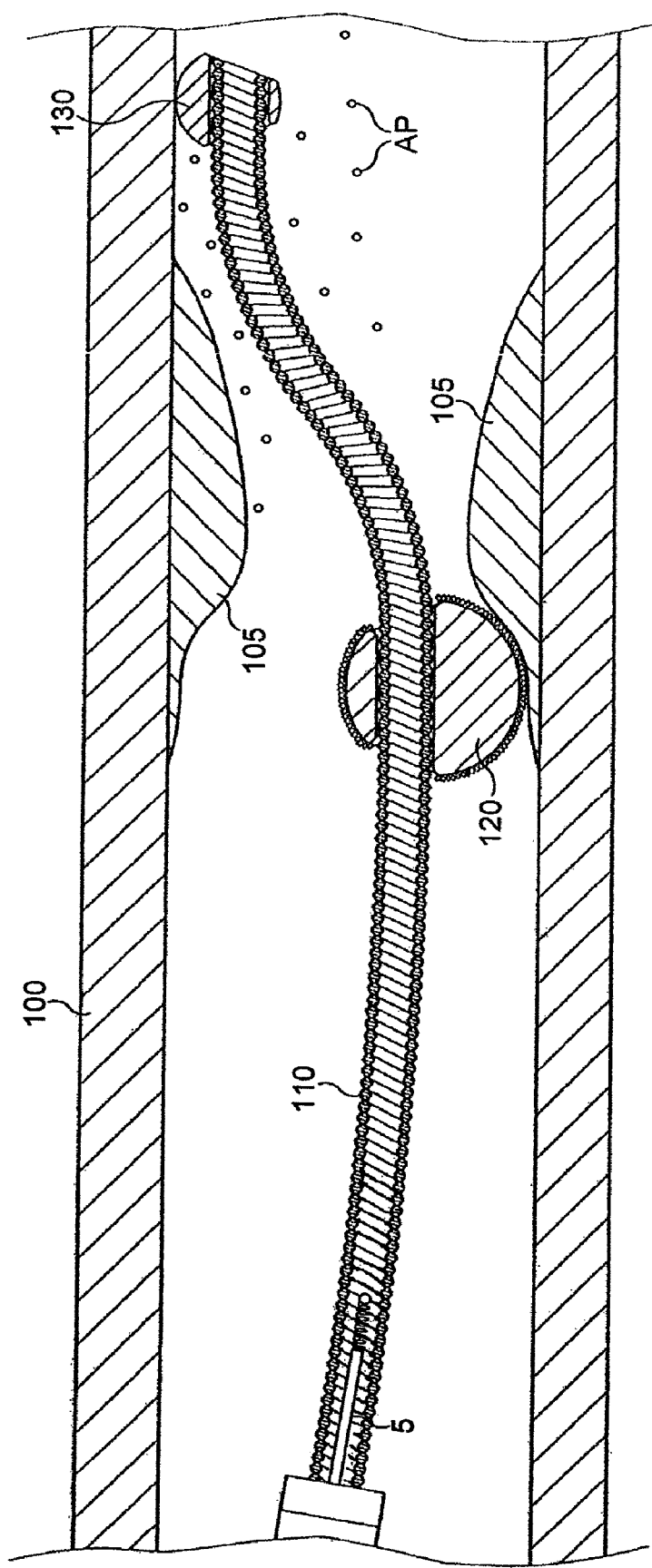
FIGS. 17-20 are successive sectional views of the device according to the invention of FIG. 12 ablating deposits in a blood vessel when the drive shaft is rotated around the guidewire which has been withdrawn into the lumen of the drive shaft such that the distal end of the guidewire is located within the lumen of the drive shaft proximal to the distal end portion of the drive shaft.
Figure 18:
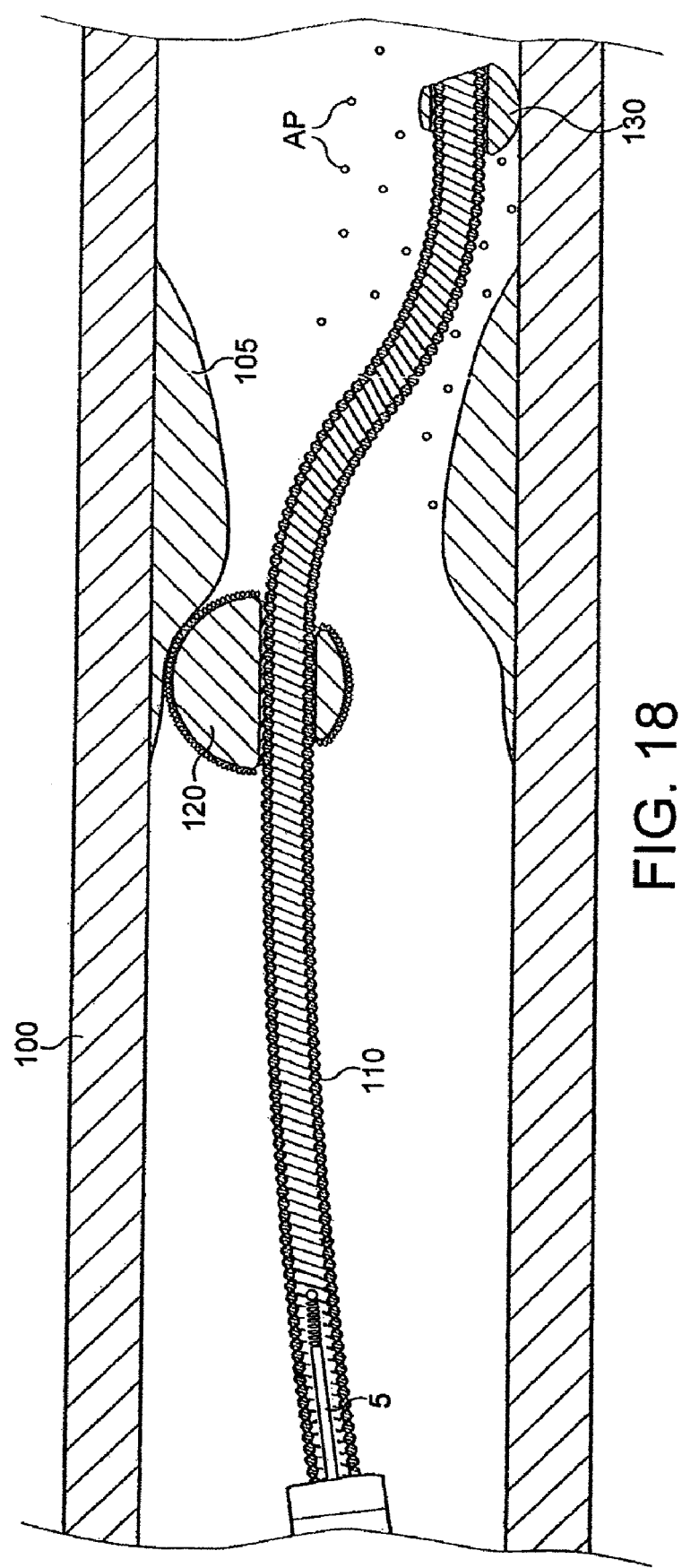
Figure 19:
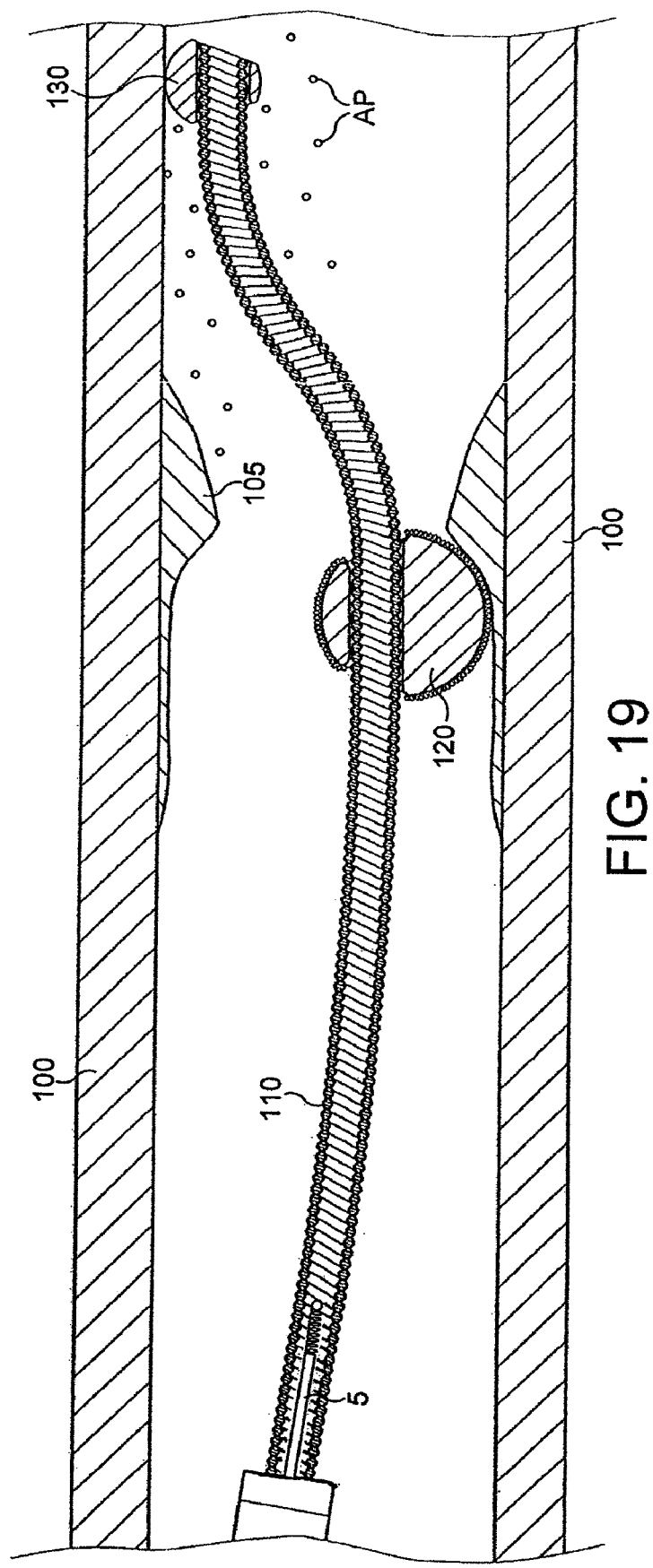
Figure 20:
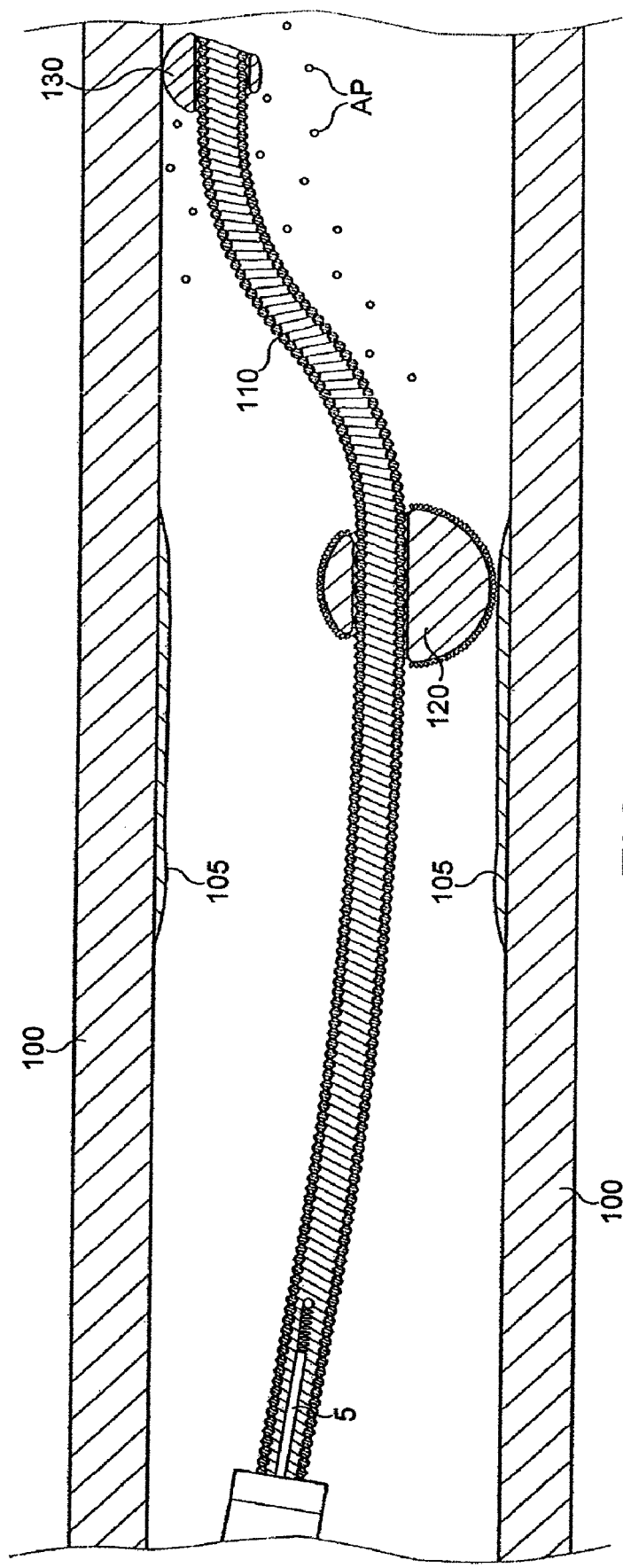

FIG. 12 depicts an alternate embodiment of the invention. Drive shaft 110 is provided with an abrasive element 120 having abrasive surface 122 and an eccentric center of mass 124 as before. However, instead of two solid counterweights, a single solid counterweight 130 having eccentric center of mass 134 is provided, preferably at the distal tip of drive shaft 110. As shown in FIGS. 13-20, drive shaft 110 will bow more gradually on the proximal side of abrasive element 120 than in the embodiment of FIGS. 4-12. FIGS. 13-16 depict the second embodiment being used in an occluded blood vessel 100 over the guidewire 5, and FIGS. 17-20 depict the second embodiment in which the guidewire 5 has been withdrawn into the lumen of the drive shaft such that the distal end of the guidewire is located within the lumen of the drive shaft proximal to the end section of the drive shaft, thereby making the distal end section of the drive shaft more flexible.

Figure 23:
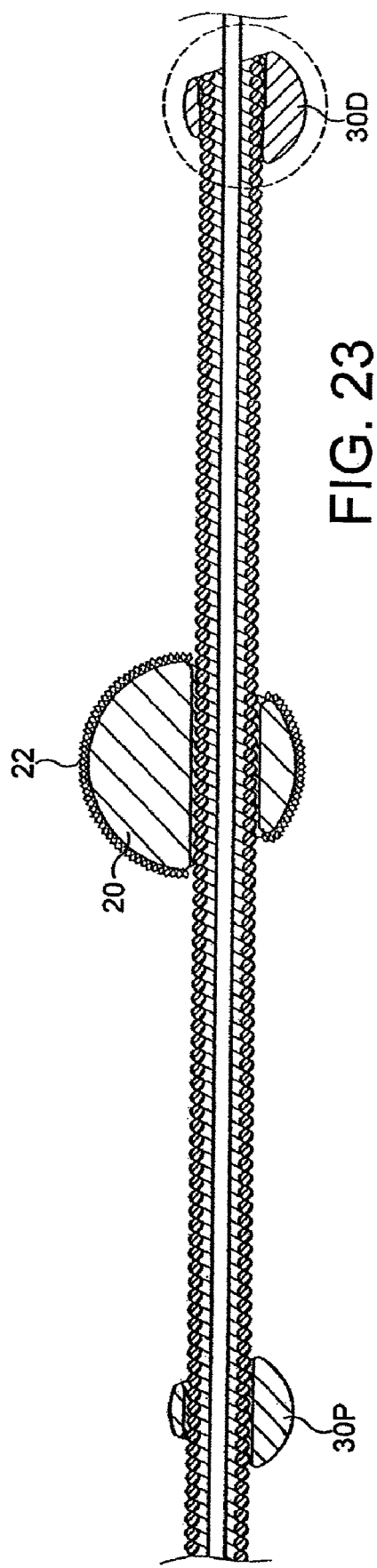
FIG. 23 is a side sectional view of another embodiment of the invention showing structure attaching the distal solid counterweight to the drive shaft.
Figure 24:
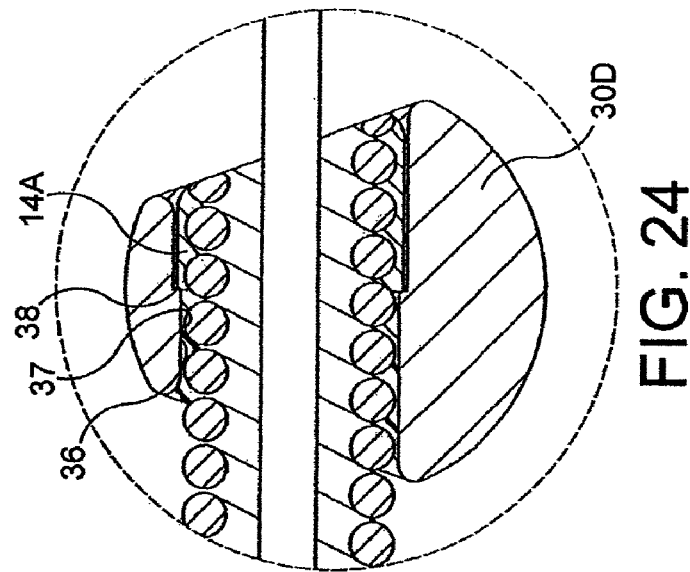
FIG. 24 is an enlarged side sectional view of the structure attaching the distal solid counterweight to the drive shaft of FIG. 23.

FIGS. 21-24 illustrate two variations in the means by which distal solid counterweight 30D is secured to drive shaft 10 (FIGS. 21 and 23 are the full views, while FIGS. 22 and 24 are enlarged views). The solid counterweight is preferably provided with a shoulder or stepped portion 38 in its internal bore 37 to become secured with adhesive 36 or other medium onto a projection or flange formed on the drive shaft 10. It will be appreciated that the solid counterweight(s) and/or the abrasive element may alternatively be attached to the drive shaft 10 by, for example, soldering or welding. The variation of FIGS. 21 and 22 includes a thin coating or layer of metal 14 formed over the wrapped wires of the drive shaft 10 which conforms in profile to the coils of drive shaft wire; consequently, layer 14 is ridged. The layer 14A of FIGS. 23 and 24 is thicker and is flat and smooth on its outer surface. In either configuration, and in others not shown, solid counterweight 30D will remain securely on the distal end of drive shaft 10.

Figure 25A:
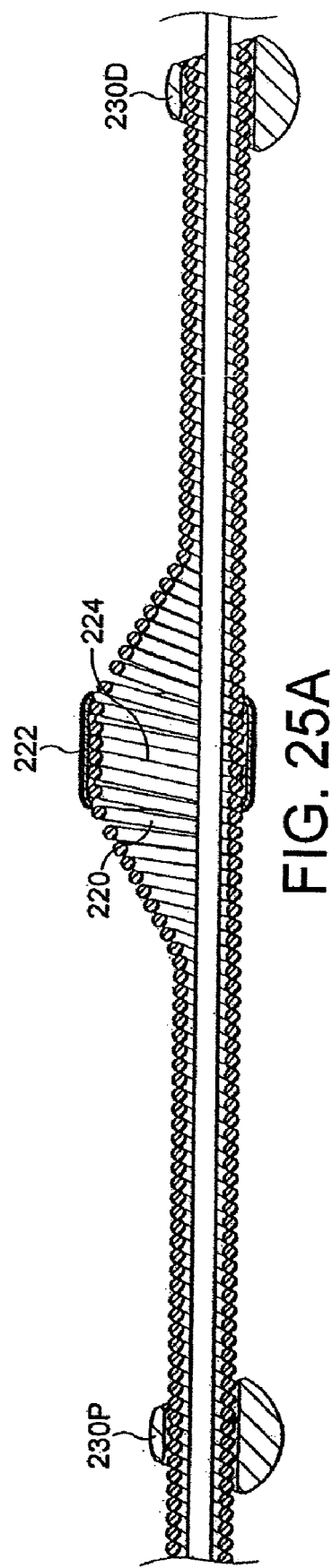
FIG. 25A is a sectional view of another embodiment of the invention where the central eccentric abrasive element is formed from windings of the drive shaft.
Figure 25B:
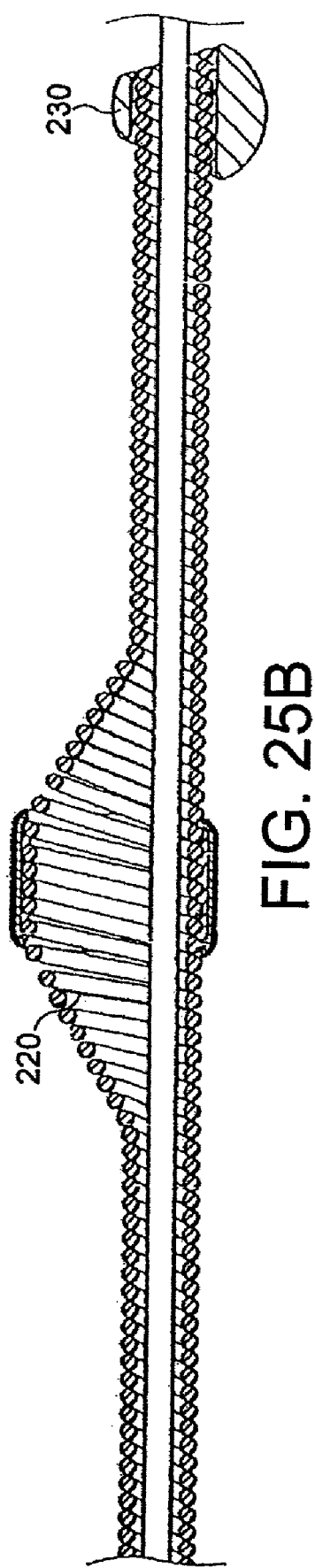
FIG. 25B is a sectional view of another embodiment of the invention having a single solid counterweight and where the central eccentric element is formed from windings of the drive shaft.
Figure 29:
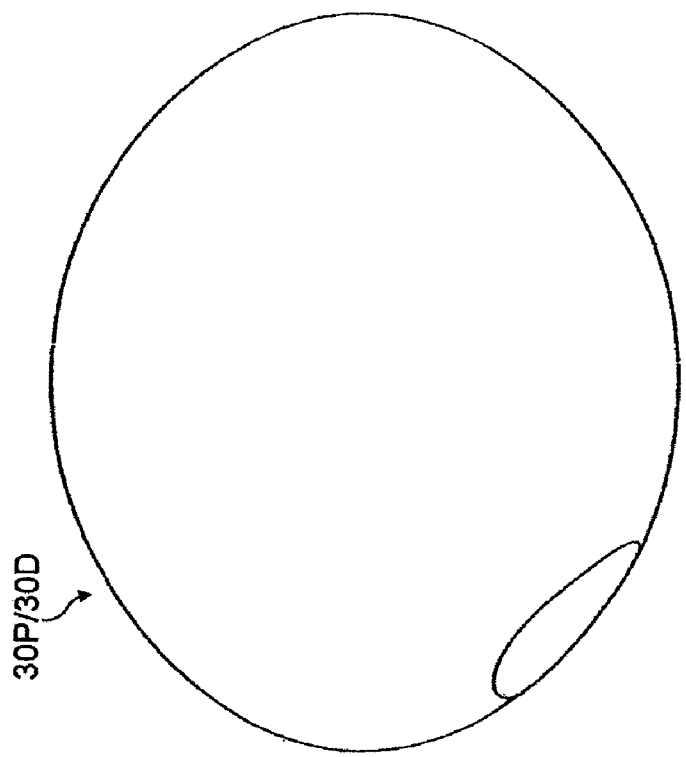
Figure 28:
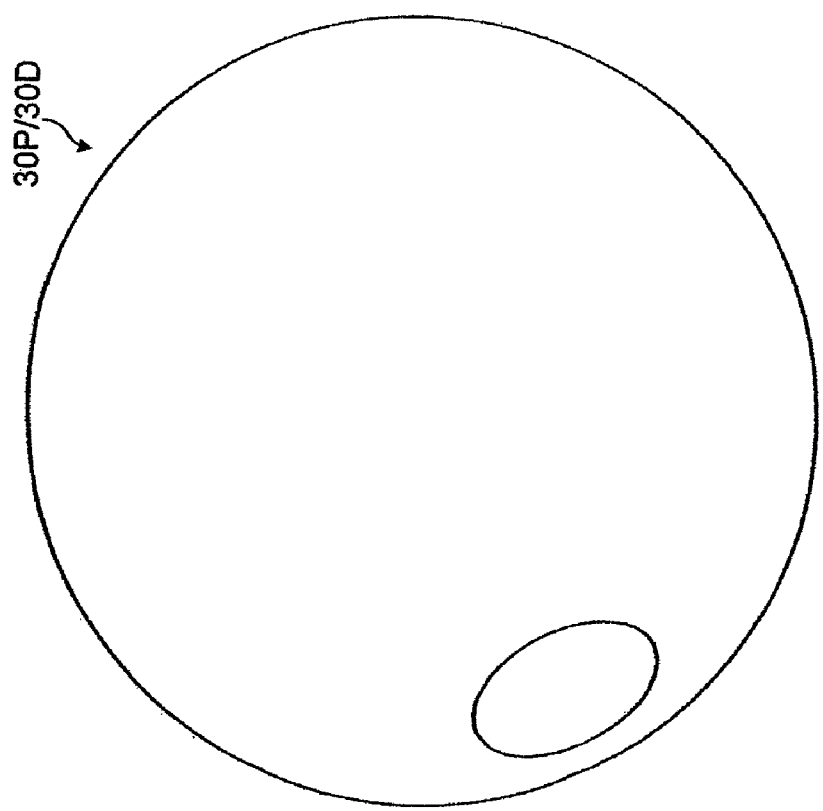

The geometries of the abrasive element and solid counterweights described above are substantially spherical. However, other configurations are also contemplated. For example, FIGS. 25A-B depict a drive shaft 210 having an abrasive element 220 which is formed from windings of the drive shaft. Abrasive element 220 is provided with abrasive surface 222 and an eccentric center of mass 224 as before. Solid counterweights 230P and D are substantially similar to solid counterweights 30P and D described above. FIG. 25B illustrates a single solid counterweight 230 associated with the abrasive element 220 of the embodiment shown in FIG. 25A. FIGS. 26 to 29 depict other shapes that may be employed for the abrasive element 20 and/or solid counterweights 30D and 30P. Any convenient shape may be employed.

The invention is not limited to the above description. For example, the abrasive element and solid counterweights are shown to be adhesively secured to the drive shaft. However, the solid counterweights and abrasive element may be secured to the drive shaft be any known means, including soldering, welding, press-fitting, and the like. Alternatively, the solid counterweights may be made of silicone and simply formed around the drive shaft. Similarly, these structures as shown are sectioned as solid metal with the heavier side (the one with the center of mass) being larger than the other side. However, there are many ways to accomplish the eccentricity of the center of mass. Some of the ways to achieve this that are contemplated as being within the scope of the invention are as follows: use two or more different materials, one heavier than the other (e.g., gold and aluminum); make one section of the solid counterweight or abrasive element hollow and the other solid; make one section hollow but fill it at least partially with a heavy material; and the like.

Also, the invention is described chiefly in context of angioplasty (primary atherectomy or restenosis), however the invention is also adaptable for use to clear any arterial or other vascular structures. Moreover, the invention is also highly suited to clear arterial or arteriovenous shunts, particularly those used for renal dialysis. The invention is not limited to biological systems either. The device may be scaled up to a more macroscopic size (e.g., inches instead of millimeters), if needed, and has utility in cleaning the insides of pipes and tubing in the chemical, aerospace, plumbing, and HVAC fields, for example.

The use of solid counterweights in the form of separate elements which are attached to the drive shaft is preferred. However, the drive shaft itself may be made with a localized eccentric weight distribution, e.g., through the eccentric wrapping of several coils of wire, to form bulges in the drive shaft that serve to counterbalance the eccentric abrasive element taught above.

The invention claimed is:

1. A rotational device, comprising:
   a flexible drive shaft having a longitudinal axis and a distal end section formed from at least one helically wound wire;
   an abrasive element attached to the distal end section, the abrasive element having a center of mass, the center of mass of the abrasive element being offset from the longitudinal axis in a longitudinal plane; and
   a distal counterweight attached to the distal end section of the flexible drive shaft at a point that is distal to the abrasive element; and
   a proximal counterweight attached to the flexible drive shaft at a point that is proximal to the abrasive element.

2. A rotational atherectomy device for removing an occlusion within a tubular structure, comprising:

a drive shaft having a distal end section formed from at least one helically wound wire;

a guidewire that is slidably receivable in a lumen of the flexible drive shaft;

a rigid abrasive element on the distal end section having a center of mass offset from a longitudinal axis of the drive shaft in a first offset direction; and distal and proximal solid counterweights fixedly secured to the at least one helically wound wire on the distal end section and spaced apart from the abrasive element such that the entire distal solid counterweight is separated from the abrasive element by a first longitudinal portion of the drive shaft extending distally of a distal end of the abrasive element and the entire proximal solid counterweight is separated from the abrasive element by a second longitudinal portion of the drive shaft extending proximally of a proximal end of the abrasive element, each of the distal and proximal solid counterweights having a center of mass offset from the longitudinal axis of the drive shaft in a second offset direction that is opposite rom the first offset direction, each of the distal and proximal solid counterweights being smaller than the abrasive element, the abrasive element having an abrasive outer surface and the distal and proximal solid counterweights having non-abrasive outer surfaces, wherein the center of mass of each of the abrasive element and the counterweights is offset from the longitudinal axis such that the distal end section of the drive shaft bows in response to rotation of the drive shaft around the guidewire while the guidewire is fully withdrawn into the lumen of the drive shaft to a position that is proximal to the abrasive element.

3. A rotational device according to claim 2, wherein each of the distal and proximal solid counterweights on the drive shaft has a weight that is about half the weight of the abrasive element.

4. A rotational device according to claim 3, wherein the distal solid counterweight being spaced distally apart from the abrasive element on the drive shaft by a distal separation distance, and the proximal solid counterweight being spaced proximally apart from the abrasive element on the drive shaft by a proximal separation distance.

5. A rotational device according to claim 4, wherein the distal separation distance is approximately equal to the proximal separation distance.

6. A rotational device according to claim 4, wherein the distal solid counterweight is disposed on the distal end of the drive shaft.

7. A rotational device according to claim 2, wherein the center of mass of at least one of the solid counterweights is generally positioned in the same longitudinal plane as the center of mass of the abrasive element.

8. A rotational device according to claim 7, wherein the center of mass of at least one of the solid counterweights is separated from the center of mass of the abrasive element by an angle of 180 degrees around the axis of the drive shaft.

9. A rotational device according to claim 2, wherein at least one of the solid counterweights has a generally spherical outer surface portion.

10. A rotational device according to claim 2, wherein at least one of the solid counterweights is substantially half the weight of the abrasive element.

11. A rotational device according to claim 2, wherein the center of mass of each of the distal and proximal solid counterweights is located in substantially the same plane as the center of mass of the abrasive element, and the center of mass of each of the distal and proximal solid counterweights is diametrically opposite to the center of mass of the abrasive element with respect to the longitudinal axis of the drive shaft.

12. A rotational device according to claim 2, wherein the distal end section of the drive shaft is flexible such that, in response to said rotation of the drive shaft, a radial profile of the distal end section of the drive shaft is substantially larger than a motionless radial profile of the distal end section of the drive shaft.

13. A rotational device according to claim 2, wherein none of the abrasive element or solid counterweights disposed on the drive shaft has a center of mass that is collinear with the drive shaft.

14. A rotational device according to claim 2, wherein an adhesive layer is arranged between the drive shaft and at least one of the solid counterweights.

15. A rotational device according to claim 2, wherein a distal end of the guidewire is smaller than a diameter of a distal opening of the lumen of the drive shaft such that the distal end of the guidewire is slidable into lumen of the drive shaft.

16. A method of using a rotational atherectomy device to remove an occlusion from inside a tubular structure, comprising the steps of:

inserting a drive shaft with an abrasive element thereon over a guidewire into a tubular structure, the abrasive element having a center of mass offset from a longitudinal axis of the drive shaft in a first offset direction, the abrasive element being spaced between distal and proximal solid counterweights on a distal end section of the drive shaft such that the entire distal solid counterweight is separated from the abrasive element by a first longitudinal portion of the drive shaft extending distally of a distal end of the abrasive element and the entire proximal solid counterweight is separated from the abrasive element by a second longitudinal portion of the drive shaft extending proximally of a proximal end of the abrasive element, each of the distal and proximal solid counterweights having a center of mass offset from the longitudinal axis of the drive shaft in a second offset direction that is opposite from the first direction;

withdrawing a distal end of the guidewire into a lumen of the drive shaft such that the guidewire is positioned proximal to the abrasive element; and after withdrawal of the distal end of the guidewire into the lumen of the drive shaft, rotating the drive shaft over the guidewire so that the offset centers of mass of the abrasive element and the counterweights cause the drive shaft to bow as the abrasive element moves in an orbital path.

17. A method according to claim 16, including the steps of:
inserting the guidewire into the tubular structure comprising a blood vessel prior to advancing the drive shaft over the guidewire into a selected position within the blood vessel to be treated.

18. A method according to claim 16, wherein the method includes the step of:

rotating the drive shaft so that the abrasive element is out of axial alignment with the distal and proximal solid counterweights after withdrawing the distal end of the guidewire into the lumen of the drive shaft.

19. A method according to claim 16, wherein the center of mass of each of the distal and proximal solid counterweights is located in substantially the same plane as the center of mass of the abrasive element, and the center of mass of each of the distal and proximal solid counterweights is diametrically opposite to the center of mass of the abrasive element with respect to the longitudinal axis of the drive shaft.

20. A method according to claim 19, wherein the step of rotating the drive shaft causes a radial profile of the distal end section of the drive shaft to be larger than a motionless radial profile of the distal end section of the drive shaft.

21. A method according to claim 16, wherein the distal solid counterweight is located on the distal end of the drive shaft.

22. A method according to claim 16, wherein none of the abrasive element or solid counterweights disposed on the drive shaft has a center of mass that is collinear with the drive shaft.

23. A method according to claim 16, wherein each of the distal and proximal solid counterweights is substantially smaller than the abrasive element, and the abrasive element has an abrasive outer surface that is different from outer surfaces of the distal and proximal solid counterweights.

24. A method according to claim 16, wherein the distal end of the guidewire is smaller than the diameter of a distal opening of the lumen of the drive shaft such that the distal end of the guidewire is slidable into lumen of the drive shaft.

* * * * *